(12) United States Patent
Shekalim

(10) Patent No.: US 8,821,474 B2
(45) Date of Patent: Sep. 2, 2014

(54) SLOW RELEASE LIQUID DRUG DELIVERY DEVICE

(75) Inventor: Avraham Shekalim, Nesher (IL)

(73) Assignee: Microsert Ltd., Yokneam Moshava (IL)

(*) Notice: Subject to any disclaimer, the term of this patent is extended or adjusted under 35 U.S.C. 154(b) by 183 days.

(21) Appl. No.: 13/430,730

(22) Filed: Mar. 27, 2012

(65) Prior Publication Data

US 2012/0184905 A1 Jul. 19, 2012

Related U.S. Application Data

(63) Continuation-in-part of application No. PCT/IB2011/050729, filed on Feb. 22, 2011, which is a continuation-in-part of application No. 12/709,525, filed on Feb. 22, 2010, now Pat. No. 8,038,650.

(60) Provisional application No. 61/468,014, filed on Mar. 27, 2011, provisional application No. 61/508,705, filed on Jul. 18, 2011, provisional application No. 61/600,648, filed on Feb. 19, 2012.

(51) Int. Cl.
*A61M 31/00* (2006.01)
*A61M 5/142* (2006.01)
*A61M 5/148* (2006.01)

(52) U.S. Cl.
CPC .......... *A61M 5/148* (2013.01); *A61M 5/14276* (2013.01); *A61M 5/14248* (2013.01)
USPC .......................................................... 604/502

(58) Field of Classification Search
USPC .......................... 604/502, 131–133, 149, 153
See application file for complete search history.

(56) References Cited

U.S. PATENT DOCUMENTS

| 3,675,658 | A | * | 7/1972 | Taylor | 604/98.01 |
| 3,677,444 | A | * | 7/1972 | Merrill | 222/135 |
| 5,080,652 | A | * | 1/1992 | Sancoff et al. | 604/132 |
| 5,219,334 | A | * | 6/1993 | Tsukada | 604/132 |

* cited by examiner

*Primary Examiner* — Nicholas Lucchesi
*Assistant Examiner* — Melissa A Snyder
(74) *Attorney, Agent, or Firm* — Mark M. Friedman

(57) ABSTRACT

A drug delivery device includes a first portion, formed primarily from elastomeric material, and a closure portion, cooperating with an opening of the first portion so as to complete an inflatable drug reservoir. The closure portion extends into the first portion inwards from the opening, defining at least one region of overlap between the first portion and the closure portion. The first portion and the closure portion define an outlet flow path for releasing a drug from the drug reservoir, with at least part of the outlet flow path passing between the first portion and the closure portion in the region of overlap. The region of overlap is disposed so as to be acted upon by a pressure within the drug reservoir thereby changing a flow impedance of the outlet flow path to provide an at least partially pressure compensated flow regulating mechanism.

18 Claims, 22 Drawing Sheets

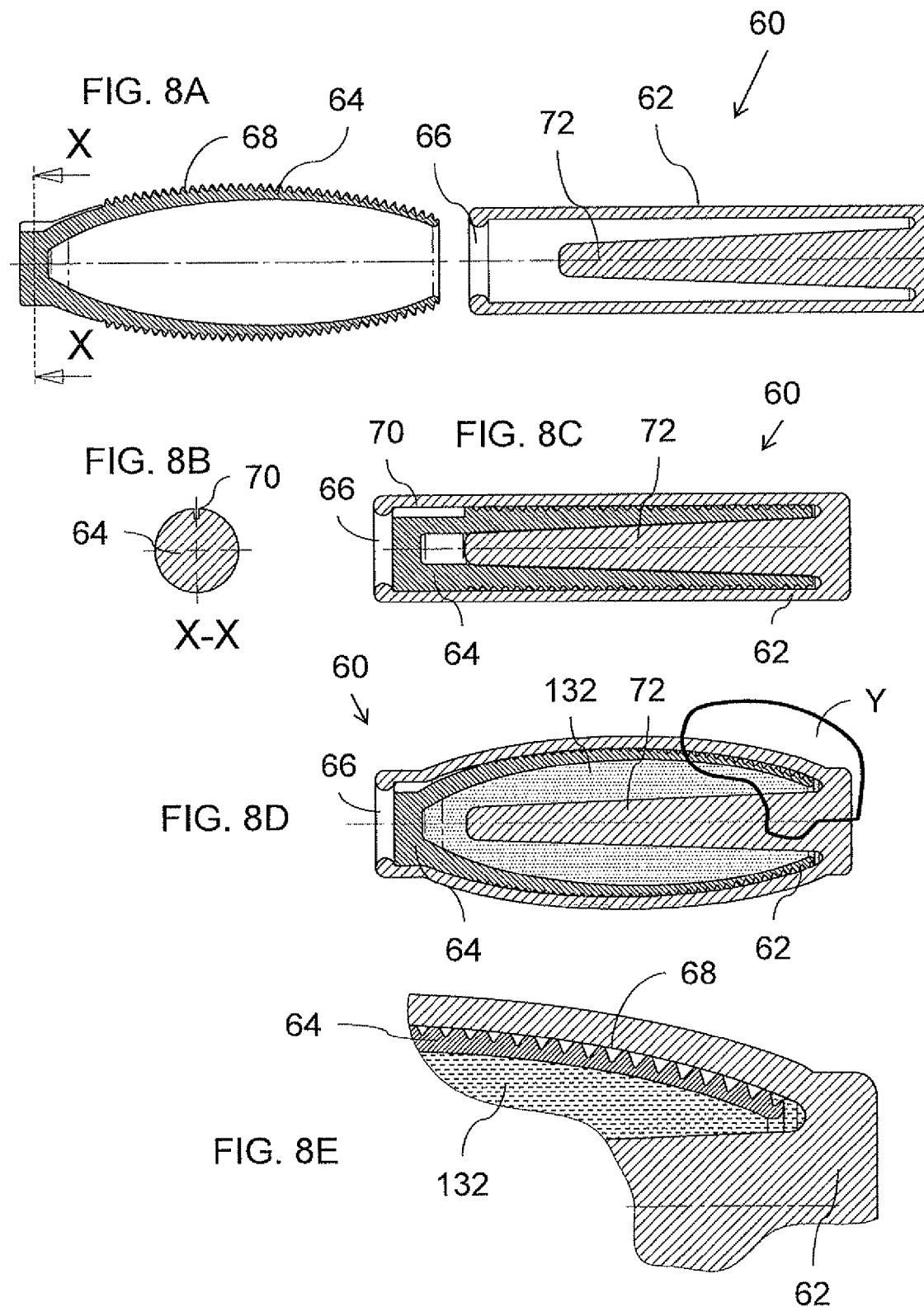

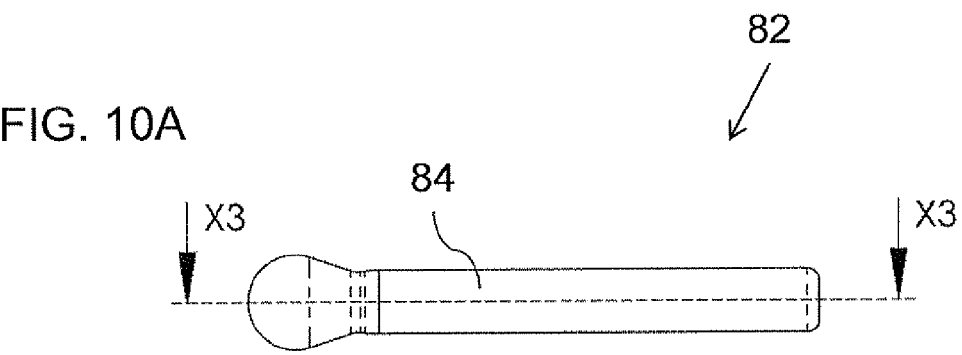
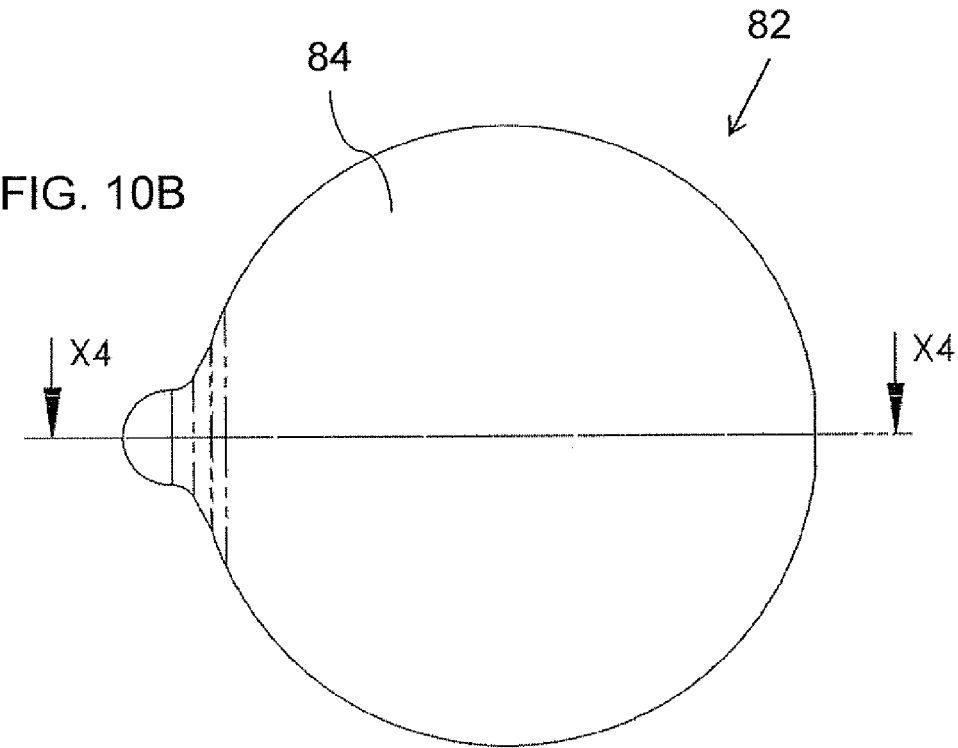

FIG. 13B
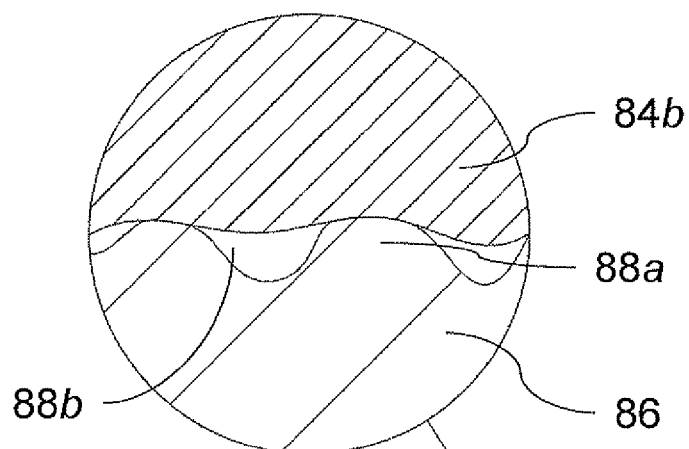
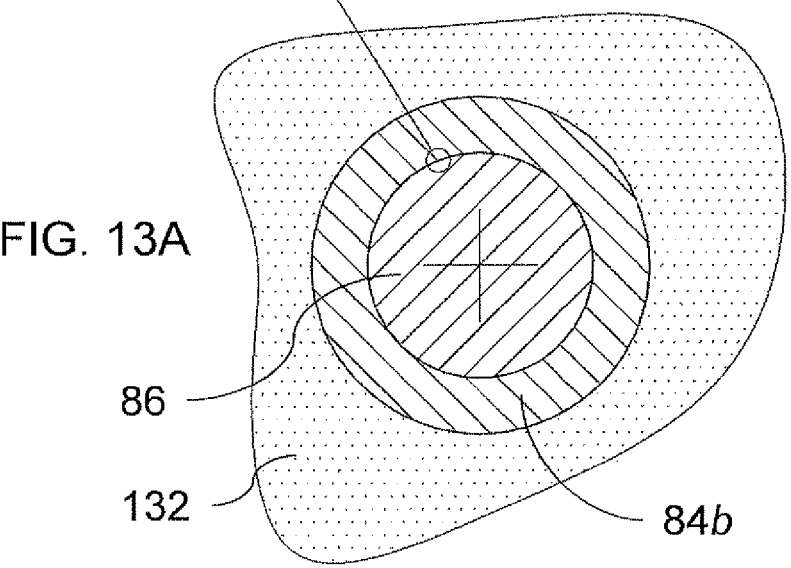
FIG. 13A

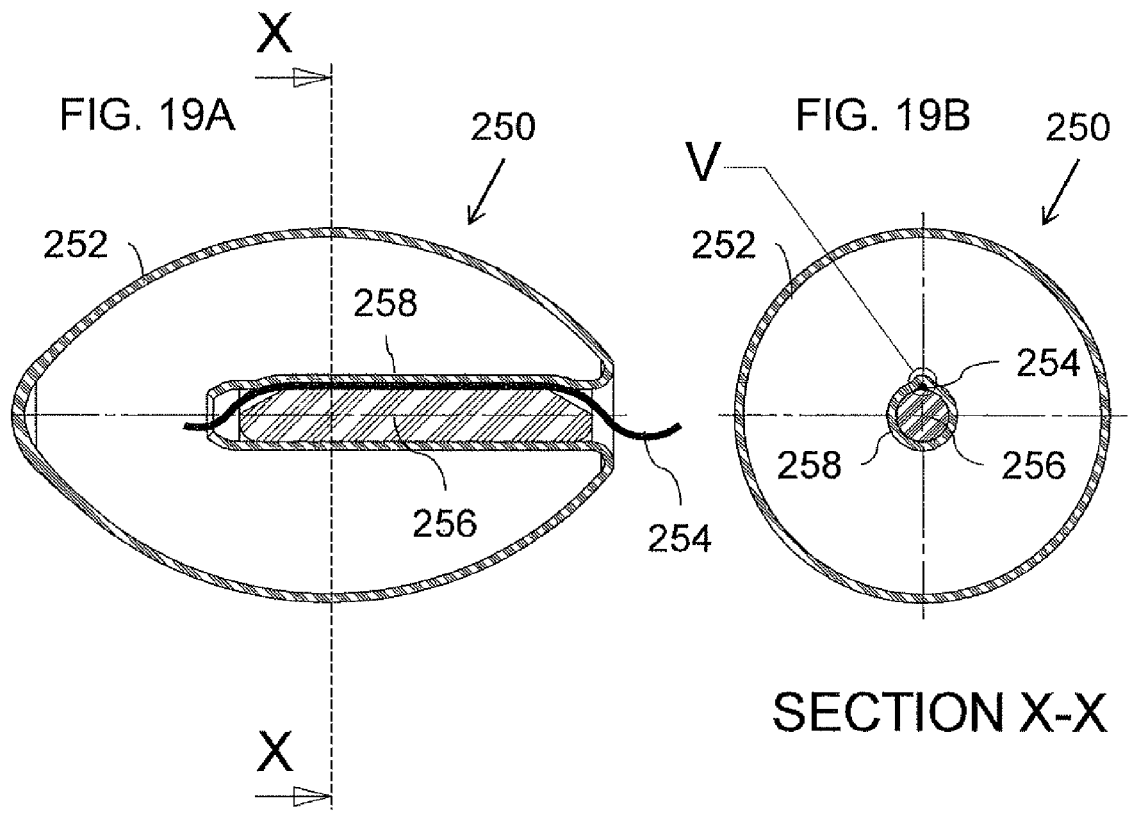
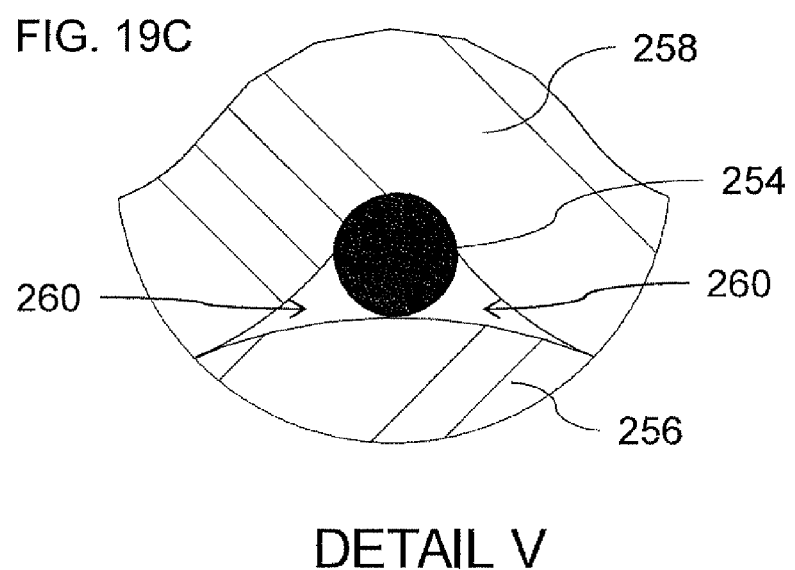

X-X

SLOW RELEASE LIQUID DRUG DELIVERY DEVICE

This is a continuation in part of Application No. PCT/IB11/050729 filed Feb. 22, 2011, which is a continuation in part of application Ser. No. 12/709,525 filed Feb. 22, 2010. This application also claims the benefit of Provisional Application Nos. 61/468,014 filed Mar. 27, 2011, and 61/508,705 filed Jul. 18, 2011, and 61/600,648 filed Feb. 19, 2012.

FIELD AND BACKGROUND OF THE INVENTION

The present invention relates to slow release liquid drug delivery devices.

It is known to provide an implantable device which delivers a drug slowly over a period of time. This approach avoids problems of patient compliance, and provides particular advantages where delivery of a drug to a specific target location allows use of much lower overall dosage than would be required for systemic delivery, possibly avoiding undesirable side effects.

Examples of implantable devices for delivery of liquid drugs include, but are not limited to, U.S. Pat. Nos. 5,163,920, 4,428,397, 4,820,273, 5,061,242, 5,993,414, 6,183,461 and 5,836,935.

There is therefore a need for an implantable drug delivery device which would deliver a liquid drug over an extended period at a relatively constant rate.

SUMMARY OF THE INVENTION

The present invention is a slow release drug delivery device for implanted or external use.

According to the teachings of an embodiment of the present invention there is provided, a drug delivery device providing a drug reservoir integrated with an at least partially pressure-compensated flow regulating mechanism, the drug delivery device comprising: (a) a first portion formed primarily from elastomeric material, the first portion at least partially defining an inflatable drug reservoir, the first portion having an opening; and (b) a closure portion cooperating with the opening of the first portion so as to complete the inflatable drug reservoir, wherein the closure portion extends into the first portion inwards from the opening to define at least one region of overlap between the first portion and the closure portion, and wherein the first portion and the closure portion define an outlet flow path for releasing a drug from the drug reservoir, at least part of the outlet flow path passing between the first portion and the closure portion in the region of overlap, the region of overlap being disposed so as to be acted upon by a pressure within the drug reservoir so as to change a flow impedance of the outlet flow path when the pressure within the reservoir varies, thereby providing an at least partially pressure compensated flow regulating mechanism.

According to a further feature of an embodiment of the present invention, at least one of the first portion and the closure portion is provided with features for defining a multi-channel flow path layer. According to one option, the features include a textured surface. According to another option, the features include a porous layer.

According to a further feature of an embodiment of the present invention, one of the first portion and the closure portion is provided with an elongated channel deployed to define at least part of the flow path through the region of overlap.

According to a further feature of an embodiment of the present invention, there is also provided a thread extending through the region of overlap such that clearance spaces around or within the thread define at least part of the flow path through the region of overlap.

According to a further feature of an embodiment of the present invention, the first portion includes a flexible sleeve extending inwards from the opening, and wherein the closure portion is implemented as an insert inserted within the flexible sleeve so as to provide the region of overlap.

According to a further feature of an embodiment of the present invention, the insert is sized to provide pre-tensioning of the inflatable drug reservoir around the insert.

According to a further feature of an embodiment of the present invention, the insert is formed primarily from a porous material.

According to a further feature of an embodiment of the present invention, the insert and the flexible sleeve are configured such that an extent of contact between the flexible sleeve and the insert varies as a function of the pressure within the inflatable drug reservoir.

According to a further feature of an embodiment of the present invention, the insert is formed with an elongated circumferential channel.

According to a further feature of an embodiment of the present invention, the insert is formed primarily from a bioresorbable material.

According to a further feature of an embodiment of the present invention, at least the first portion is formed from silicone.

According to a further feature of an embodiment of the present invention, at least one of the first portion and the closure portion is formed from a bioresorbable material.

According to a further feature of an embodiment of the present invention, the first portion and the closure portion are formed as two separate components.

According to a further feature of an embodiment of the present invention, the first portion and the closure portion are integrally formed, and wherein the drug delivery device is assembled by inverting at least one sleeve-like portion so as to generate the region of overlap.

According to a further feature of an embodiment of the present invention, the region of overlap forms part of an outer wall of the inflatable drug reservoir.

According to a further feature of an embodiment of the present invention, there is also provided a central core deployed within the inflatable drug reservoir and sized to provide pre-tensioning of the inflatable drug reservoir around the central core.

According to a further feature of an embodiment of the present invention, the central core is integrally formed with at least one of the first portion and the closure portion.

According to a further feature of an embodiment of the present invention, there is also provided a septum integrated with the first portion for piercing by a needle during filling of the inflatable drug reservoir, wherein the septum projects into the inflatable drug reservoir.

BRIEF DESCRIPTION OF THE DRAWINGS

The invention is herein described, by way of example only, with reference to the accompanying drawings, wherein:

FIG. 8A is a schematic cross-sectional view taken through two components ready for assembly to form a drug delivery device according to an embodiment of the present invention;

FIG. 8B is a cross-sectional view taken along line X-X of FIG. 8A;

FIGS. 8C and 8D are schematic cross-sectional views taken through a drug delivery device according to an embodiment of the present invention assembled from the components of FIG. 8A, showing the device in its empty and filled states, respectively;

FIG. 8E is an enlarged view of the region of FIG. 8D designated Y;

FIGS. 10A and 10B are side views of a drug delivery device according to an embodiment of the present invention, shown in an empty and a full state, respectively;

FIG. 13A is a cross-sectional view taken along line X5-X5 of FIG. 12A;

FIG. 13B is a further enlarged view of a circular region of FIG. 13A as indicated;

FIG. 19A is a schematic cross-sectional view of a drug delivery device based upon use of a thread to define a narrow flow passageway, constructed and operative according to an embodiment of the present invention;

FIG. 19B is a schematic cross-sectional view taken along the line X-X in FIG. 19A;

FIG. 19C is an enlarged view of the region of FIG. 19B designated V;

DESCRIPTION OF THE PREFERRED EMBODIMENTS

An embodiment of the present invention is a drug delivery device with a particularly simple construction, typically formed from a total of only three, or in some cases two, components. In certain cases, the device may even be assembled from a single component.

Before addressing a number of specific non-limiting examples, in general terms, an embodiment of the present invention provides a drug delivery device that integrates a drug reservoir with an at least partially pressure-compensated flow regulating mechanism in a particularly simple and compact structure. The device includes a first portion, formed primarily from elastomeric material, which at least partially defines an inflatable drug reservoir, and a closure portion, cooperating with an opening of the first portion so as to complete the inflatable drug reservoir. The closure portion extends into the first portion inwards from the opening, defining at least one region of overlap between the first portion and the closure portion.

The first portion and the closure portion define an outlet flow path for releasing a drug from the drug reservoir, with at least part of the outlet flow path passing between the first portion and the closure portion in the region of overlap. The region of overlap is disposed so as to be acted upon by a pressure within the drug reservoir so as to change a flow impedance of the outlet flow path when the pressure within the reservoir varies, thereby providing an at least partially pressure compensated flow regulating mechanism.

Figure 1A:
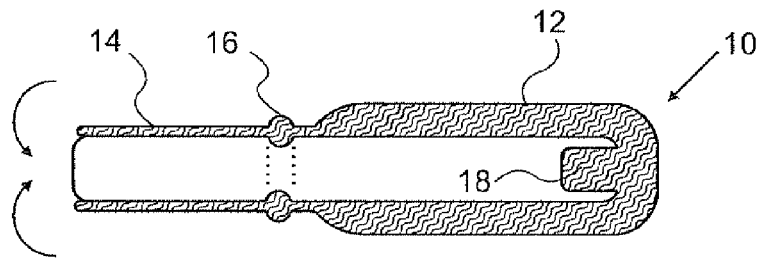
FIG. 1A is a schematic cross-sectional view taken through a bladder-type reservoir from an implantable drug delivery device according to an embodiment of the present invention.
Figure 1B:
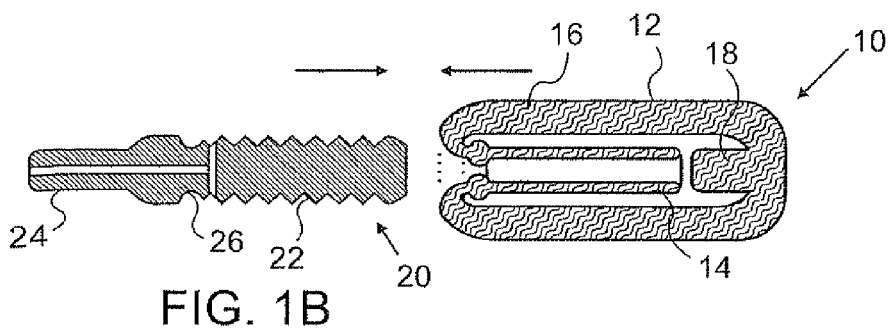
FIG. 1B is a schematic cross-sectional view taken through the bladder-type reservoir of FIG. 1A and an insert for use in an implantable drug delivery device according to an embodiment of the present invention.
Figure 1C:
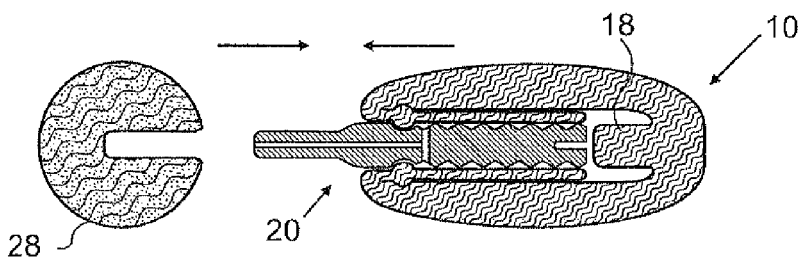
FIG. 1C is a schematic cross-sectional view taken through the bladder-type reservoir and insert of FIG. 1B after assembly, and showing an outlet diffuser for use as part of an implantable drug delivery device according to an embodiment of the present invention.
Figure 1D:
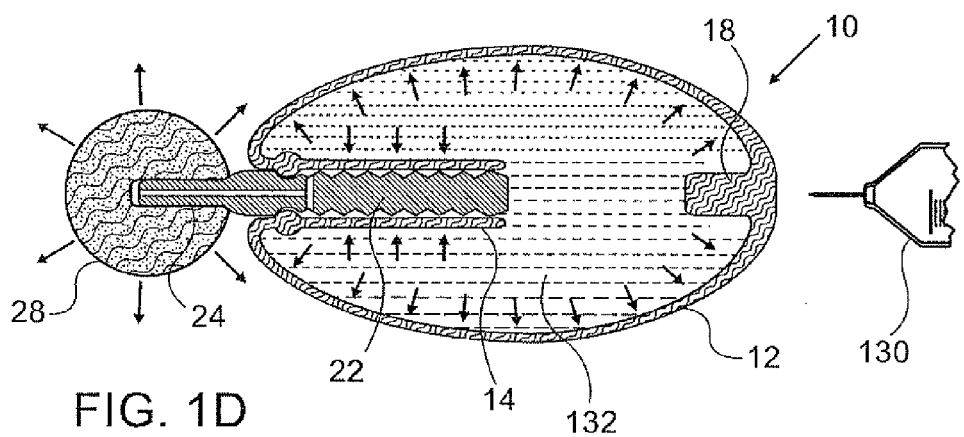
FIG. 1D shows the implantable drug delivery device assembled from the components of FIG. 1C after being filled with a liquid drug.
Figure 2:
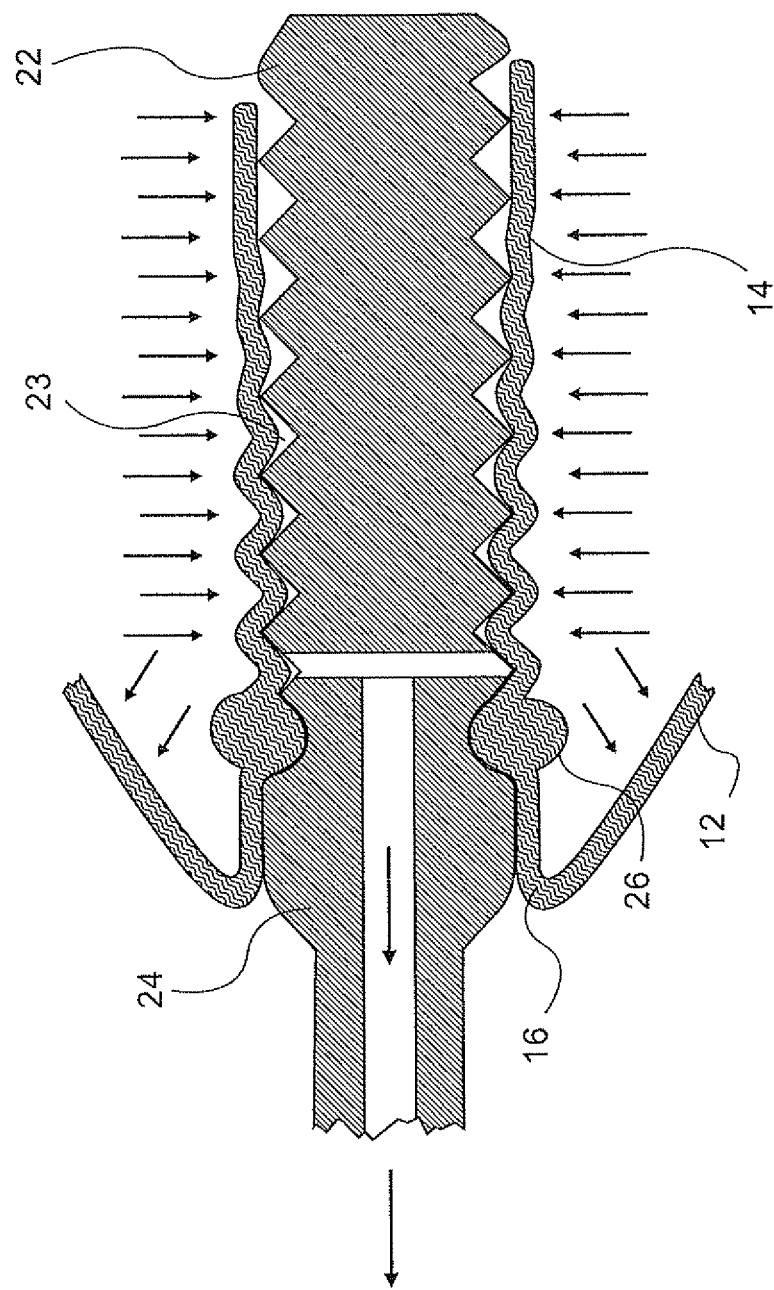
FIG. 2 is an enlarged region of FIG. 1D illustrating a flow regulation/compensation mechanism according to an embodiment of the present invention.

An embodiment of the device illustrated in FIGS. 1A-2 is formed from a first portion, implemented as an elastomeric component 10, which is formed with an inflatable bladder-type reservoir 12 and a regulator sleeve 14. In the preferred case illustrated here, elastomer component 10 also has an integrated retainer bead 16 which defines an opening of reservoir 12 and a thickened portion defining a pierceable septum 18 for filling or refilling the device.

A second component, the closure portion, is here implemented as an insert 20 which is configured to cooperate with regulator sleeve 14 to define a pressure-compensated flow restriction, thereby regulating a rate of drug release from the device to a relatively constant rate. In the example shown here, insert 20 has a regulator portion 22 formed with a variable geometry helical flow channel 23, described below in more detail with reference to FIG. 2, and an outlet portion 24 defining a flow outlet. A peripheral groove 26 is provided to receive retainer bead 16.

A third component of the device illustrated here is an outlet diffuser 28 in the form of a porous body, here shown as a sphere, which is configured to attach to outlet portion 24.

The drug delivery device is assembled by folding regulator sleeve 14 inwards inside reservoir 12 and introducing insert 20 until retainer bead 16 engages groove 26 to produce the configuration shown in FIG. 1C. Outlet diffuser 28 is attached to complete the device. The device can then be filled (and subsequently refilled) via a needle (shown schematically as syringe 130 in FIG. 1D) inserted through septum 18 to inflate reservoir 12 with a liquid 132 to be delivered. The elasticity of the reservoir acts like a balloon to apply pressure to the contained liquid, thereby driving release of the liquid through the flow regulation mechanism.

In certain particularly preferred embodiments, as illustrated here, septum 18 is formed and positioned so that at least part of the septum projects inwards into reservoir 12. The exposure of the inwardly-projecting part of septum 18 to the pressure within the reservoir tends to help achieve resealing of the path along which a filling needle was inserted. It will be noted that septum 18 may be implemented as a thickened integral part of the wall forming reservoir 12, or may be a separate element which is sealingly attached to the reservoir wall by any suitable bonding technique.

According to one non-limiting embodiment, inflatable reservoir 12 may be configured to maintain a relatively constant pressure over a majority of its design volume, as is known in the art. However, the self-compensating flow regulation described herein renders this feature non-critical.

Most preferably, the relaxed state of reservoir 12 closes closely against the regulation mechanism formed by the region of overlap between sleeve 14 and regulator portion 22, thereby ensuring a driving pressure for delivering the drug until the reservoir is substantially empty.

Operation of the flow regulation mechanism of this embodiment is best understood with reference to FIG. 2. Helical flow channel 23 together with the inward facing surface of sleeve 14 define an elongated helical channel. Pressure within the reservoir (resulting from the resilient contracting force exerted by the elastomer outer walls) acts on the regulator sleeve 14, trying to force the elastomer sleeve into channel 23. In the region of channel 23 near the beginning of the flow path through the regulation mechanism, the pressure difference between the flow channel and the reservoir pressure is small and only a small deformation of regulator sleeve 14 occurs. As the liquid continues along the long helical path, the pressure gradually drops, leading to a larger pressure differential across the sleeve and tending to conform the sleeve closer to the channel shape. It will be noted that, if the pressure within the reservoir increases, such as from something pressing against the reservoir, sleeve 14 becomes pressed more closely into channel 23 thereby constricting the flow path and compensating for the increased reservoir pressure to maintain a relatively constant outlet flow rate. Conversely, if the reservoir pressure decreases, such as from a drop in ambient pressure at high altitude, sleeve 14 is pressed less closely into channel 23, instead resiliently returning towards its relaxed cylindrical state and thereby reducing constriction of the flow path. In this manner, the flow rate is compensated, rendering it relatively constant under conditions of varying reservoir pressure.

Helical flow channel 23 is shown here as a uniform cross-section channel. However, it will be noted that channel 23 may optionally be formed with a variable depth and/or shape along its length so as to modify and improve the uniformity of the flow compensation. For example, in some cases, it may be desirable that the region closer to the inlet end (the right hand side as shown in FIG. 2) is deeper and/or narrower and the channel 23 becomes progressively shallower and/or wider towards the outlet.

Optionally, channel 23 may be shaped to help ensure that the flow path does not become completely sealed, for example, by employing a sharply angled root to the channel. However, it should be noted that this feature is not essential. As already explained, regulation is achieved as a result of pressure difference between the reservoir and the flow path. In any situation where the flow path were to become momentarily blocked, the static pressure along the flow path up to the blockage would quickly equalize, thereby applying the full intra-reservoir pressure directly at the point of blockage so as to clear the blockage. As a result, self-blocking of the regulation mechanism is typically avoided in all cases.

It is a particularly preferred feature of certain implementations of the present invention that the device need not be surgically removed on completion of its drug delivery function. To this end, part or all of the device may be made from bioresorbable materials which degrade over time and are absorbed into the body tissue or otherwise disposed of by natural body processes. In particular, certain preferred implementations have insert 20 and/or outlet diffuser 28 formed from bioresorbable material. Examples of suitable bioresorbable materials include, but are not limited to biodegradable polymers such as poly(lactic acid), poly(glycolic acid), poly (ortho ester), and polyanhydrids, as well as copolymers of these materials. Clearly, the rate of degradation must be chosen to be slow relative to the planned functional lifetime of the device. Choice of a suitable composition with a corresponding degradation rate suitable for any given implementation is well within the skill of one ordinarily skilled in the art.

Regarding production of porous polymer materials from biodegradable and other polymer materials, various production techniques and corresponding products are commercially available. Examples of commercial sources for such materials include, but are not limited to, Porex Technologies Inc. (GA, USA) and MicroPore Plastics Inc. (GA, USA).

Where insert 20 and outlet diffuser 28 are formed from biodegradable materials, elastomeric component 10 may be formed from an inert non-biodegradable material such as silicone rubber. The empty squashable structure of the collapsed reservoir remaining after full degradation of the other components is believed to be physiologically acceptable when left subcutaneously for an indefinite period.

Alternatively, elastomeric component 10 may also be formed from a biodegradable elastomer to provide a fully biodegradable product. Non-limiting examples of suitable bioresorbable elastomers are poly(glycerol-sebacic acid) ("PGS"), polycaprolactone (PCL), PLC (70L/30C) (L-lactide/ε-caprolactone) and/or polylactide (PLA) based elastomers. The aforementioned materials are commercially available from a number of sources, such as for example Zeus, Absorv®—Bioabsorbables (Orangeburg, CS, USA).

Although illustrated here in a preferred implementation in which reservoir 12 and sleeve 14 are integrated as part of a single elastomeric component, alternative embodiments in which reservoir 12 and sleeve 14 are separate elements subsequently fastened together or clamped together during use also fall within the scope of the present invention.

Furthermore, although illustrated here in a preferred implementation in which flow regulation is performed by deformation of sleeve 14 against insert 20, alternative embodiments in which a self-contained flow regulator (not shown) is inserted within sleeve 14 and sleeve 14 itself does not perform an active role in the flow rate regulation also fall within the scope of the present invention.

Figure 3:
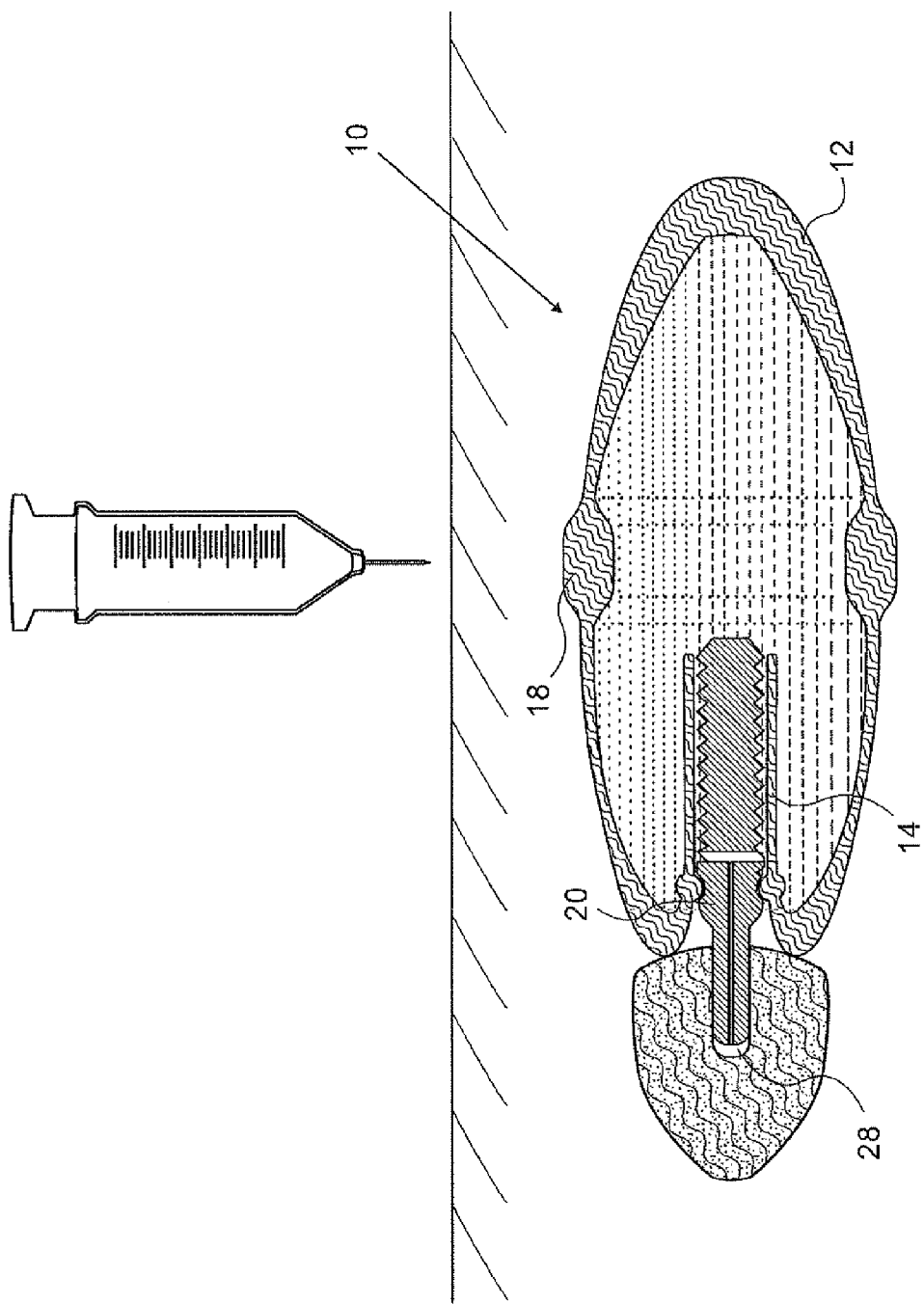
FIG. 3 illustrates a variation of the implementation of FIG. 1D which allows percutaneous refilling of the reservoir while lying transversely beneath the skin of a patient.

Turning now to FIG. 3, this shows a device similar to the device of FIGS. 1A-2, but formed in an elongated shape suitable for implanting lying flat under the skin. To facilitate percutaneous refilling of the device, the device is here formed with a thickened annular septum as a belt around the reservoir, thereby allowing tactile location of the septum and lateral injection directly into the reservoir. In all other respects, the device of FIG. 3 is structurally and functionally analogous to the device of FIGS. 1A-2.

Figure 4:
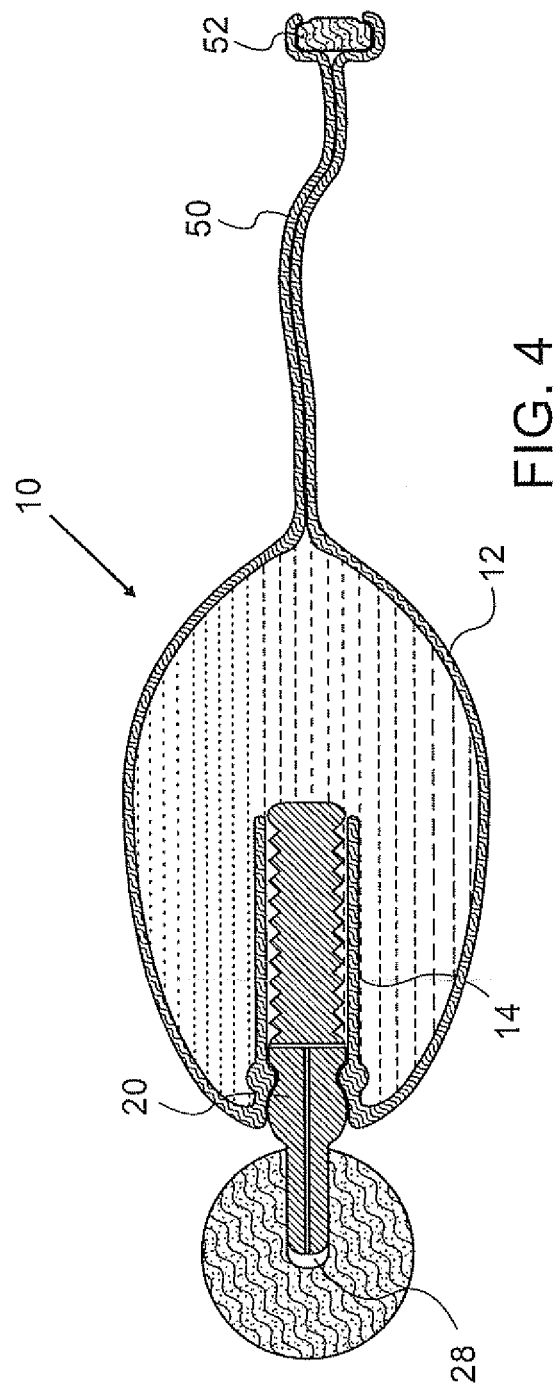
FIG. 4 illustrates a further variation of the implementation of FIG. 1D in which the reservoir is integrally formed with a filling tube that terminates in a remote septum, allowing percutaneous refilling of the reservoir for a drug delivery device deployed in an inaccessible location within the body of a patient.

Turning now to FIG. 4, this shows a device similar to the device of FIGS. 1A-2, but in which the inflatable bladder-type reservoir is integrally formed with a filling tube 50 which terminates in a refilling port with a septum 52. By suitable choice of wall thickness and tube diameter, it is possible to form the refilling tube from the same elastomer material as used for the reservoir while ensuring that it does not dilate under the pressures used to inflate the reservoir with a drug. As a result, substantially all of a drug injected through the refilling septum is transferred directly into the reservoir. This configuration allows deployment of the drug delivery device in proximity to a deep body target region while maintaining percutaneous accessibility for refilling. The parts of the device are typically secured in situ by appropriate stitching of adjacent tissue, as is well known in the art. In all other respects, the device of FIG. 4 is structurally and functionally analogous to the device of FIGS. 1A-2.

Figure 5:
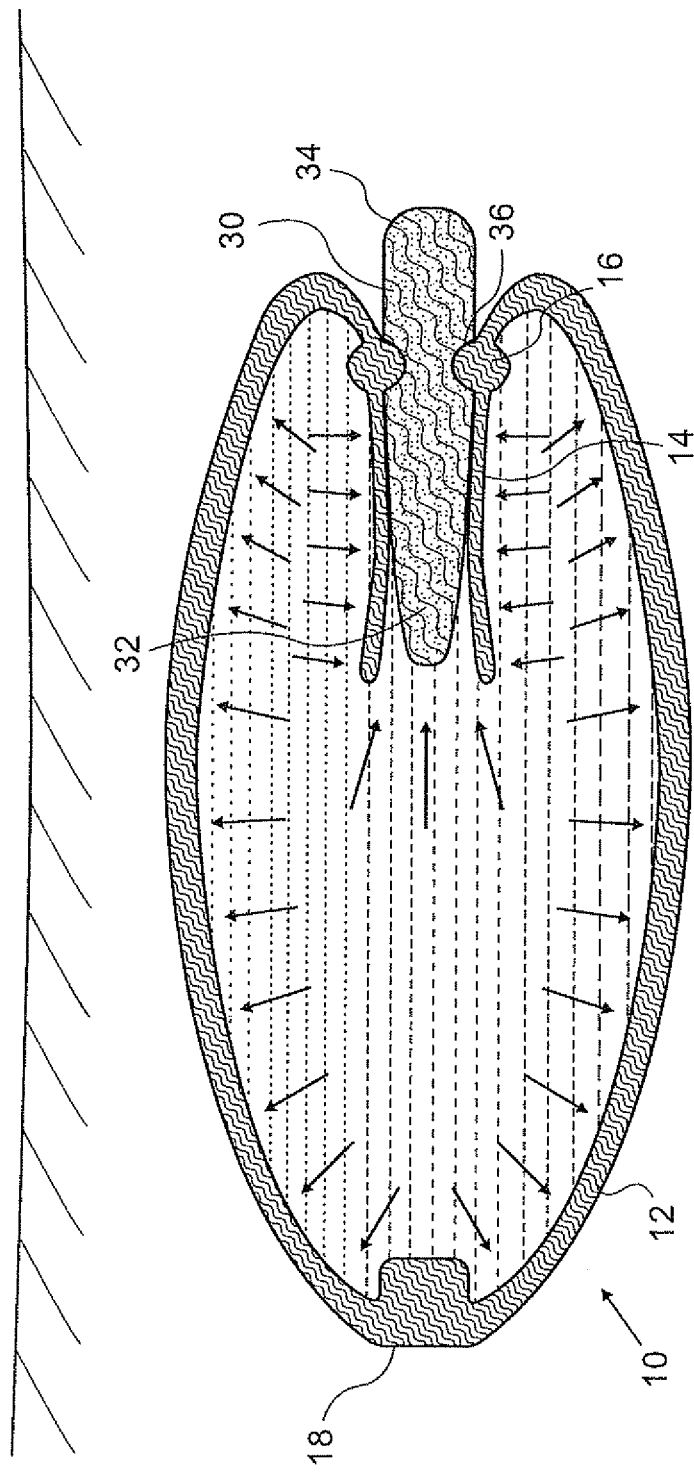
FIG. 5 illustrates an implantable drug delivery device according to an alternative embodiment of the present invention employing a porous insert as part of a flow compensation mechanism.
Figure 6:
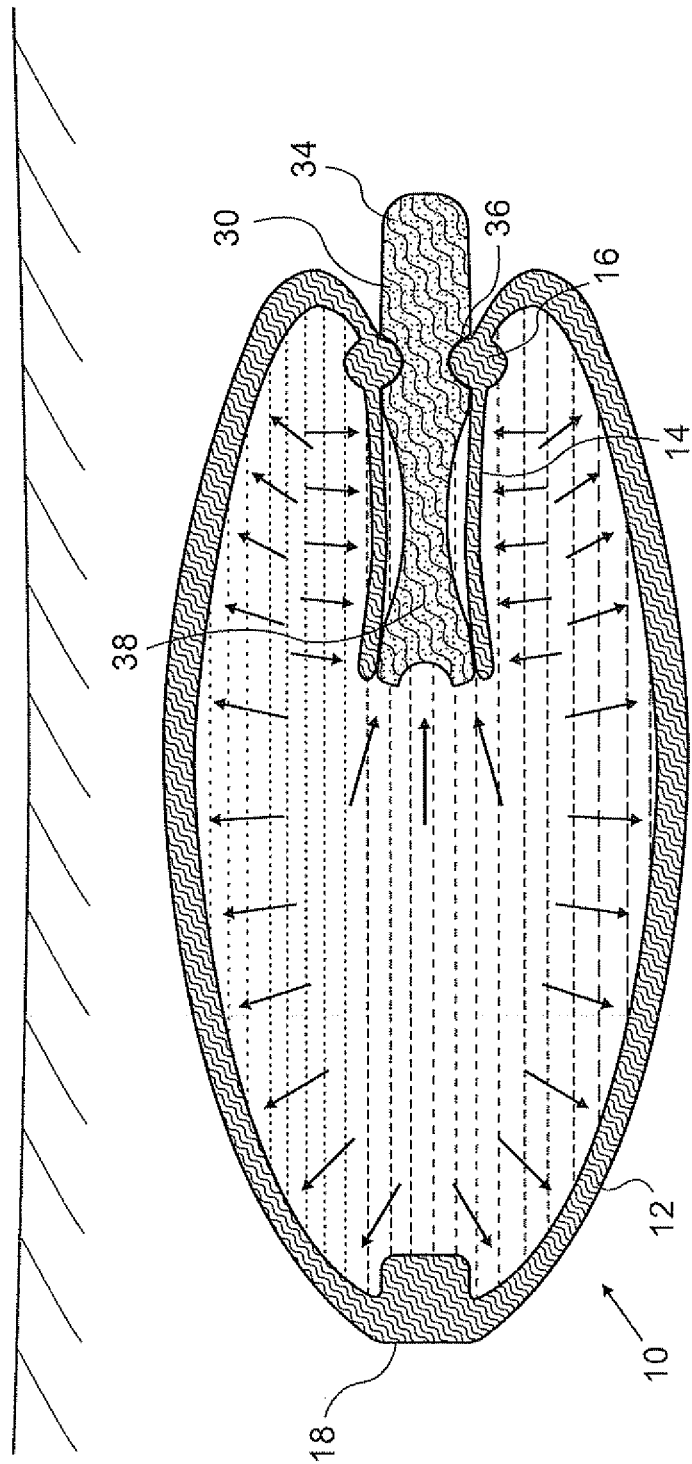
FIG. 6 illustrates an embodiment similar to FIG. 5 but employing a variant form of the porous insert.
Figure 7:
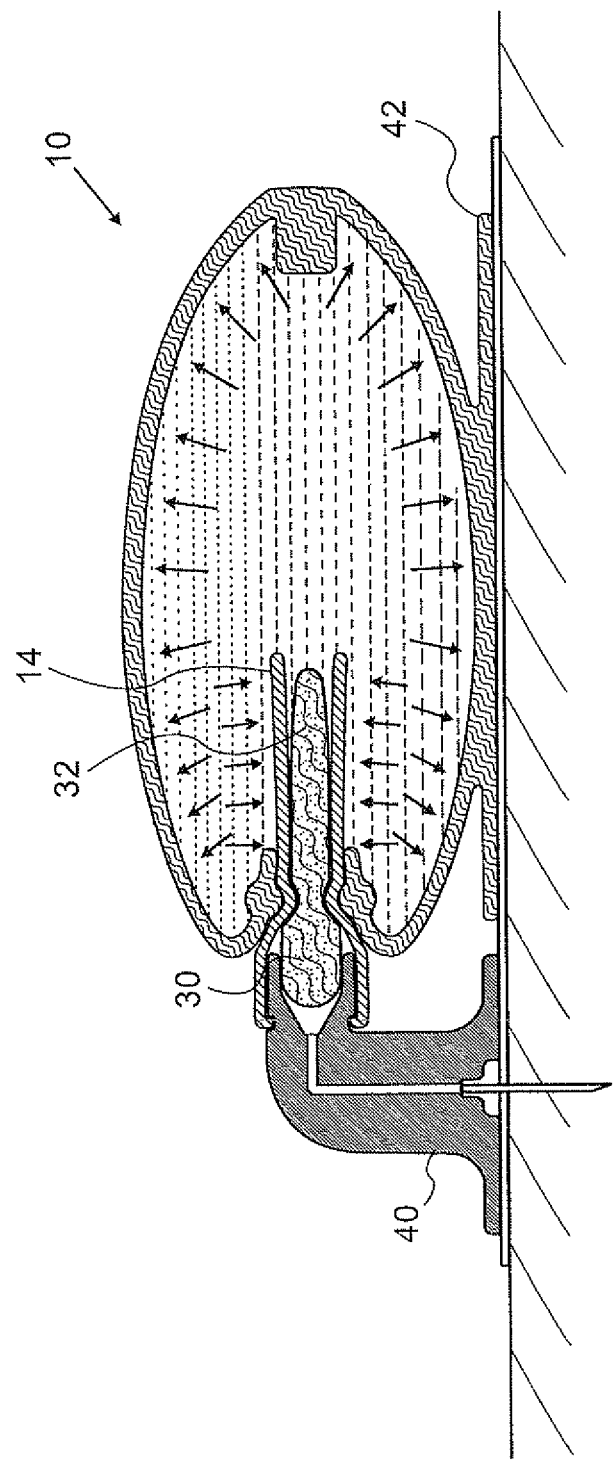
FIG. 7 illustrates a modified embodiment of the present invention for use as an external drug delivery device.
Figure 9A:
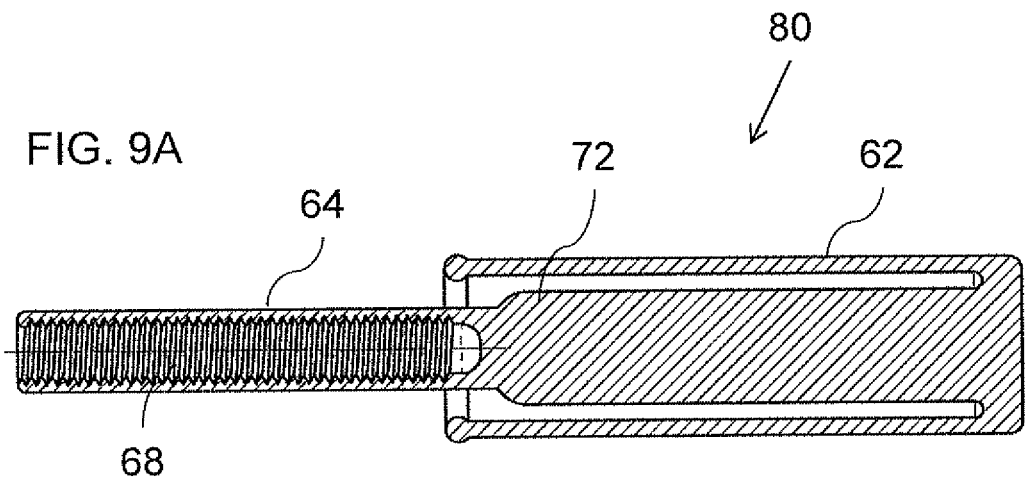
FIG. 9A is a schematic cross-sectional view taken through a single-piece drug delivery device according to an embodiment of the present invention prior to assembly.
Figure 9B:
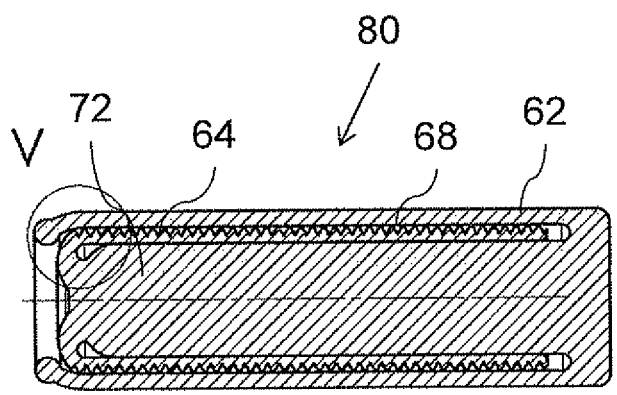
FIGS. 9B and 9C are schematic cross-sectional views taken through the drug delivery device of FIG. 9A after assembly, showing the device in its empty and filled states, respectively.
Figure 9D:
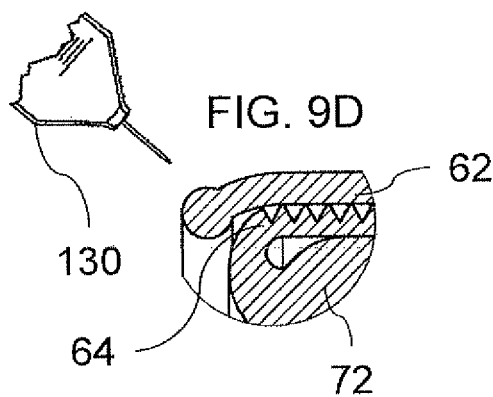
FIG. 9D is an enlarged view of the region of FIG. 9B designated V.
Figure 9C:
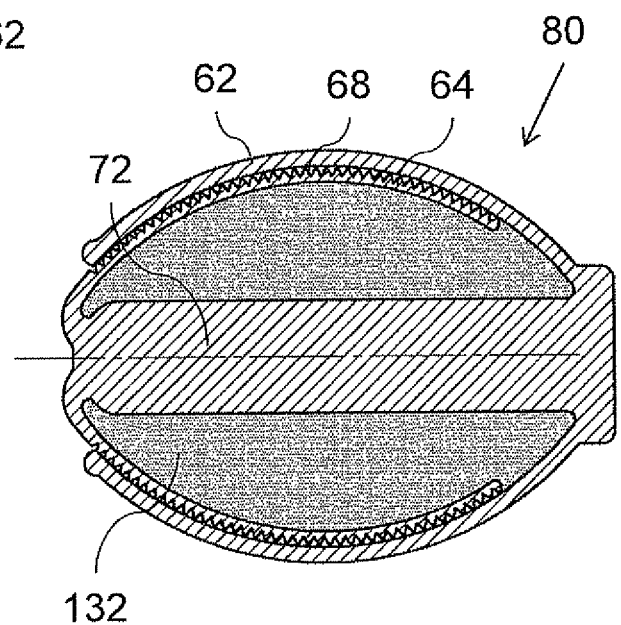

Turning now to FIGS. 5 and 6, there are shown additional embodiments of a drug delivery device according to an aspect of the present invention. These devices are conceptually and structurally similar to the devices described above, but employ a porous insert to define at least part of the flow regulation mechanism. Specifically, referring first to FIG. 5, there is shown a device in which the first portion is implemented as an elastomeric component 10 essentially the same as described earlier (including inflatable bladder-type reservoir 12, regulator sleeve 14, integrated retainer bead 16 and pierceable septum 18). In this case, insert 20 described above is replaced by a closure portion implemented as a porous insert 30 which has a generally conical regulating portion 32, an outlet portion 34 and a peripheral groove 36. The porous material of insert 20 provides a flow restriction, defining a limited rate of release of the liquid contents of reservoir 12. Flow regulation is achieved by pressure-responsive closing or opening of regulator sleeve 14 against the surface of the conical regulating portion, thereby forcing the liquid flow to pass through a longer or shorter path via the porous material as a function of the pressure differential between the reservoir and liquid along the flow path.

FIG. 6 shows a similar device in which regulating portion 38 of porous insert 30 has a generally hour-glass shape, ensuring that there is a significant initial pressure drop near the beginning of the flow path through the porous material. Here too, flow regulation/compensation is achieved by the pressure differential causing a variable degree of closure of the regulator sleeve against the narrower portion of the insert, thereby defining a relatively longer or shorter length of flow path along which the flow can bypass the porous material and find a lower flow impedance path.

It should be noted that, in all other respects, the embodiments of FIGS. 5 and 6 are similar to the previously described embodiments, and can be implemented with any and all of the various features described above with reference to FIGS. 1-4. Similarly, these embodiments can be implemented as partially or fully resorbable structures. Typically, due to the inherent diffuse release properties of the porous insert 30, no additional outlet diffuser is required.

Turning now to FIGS. 8A-8E, these illustrate various aspects of a drug delivery device, generally designated 60, constructed and operative according to a further embodiment of the present invention. Device 60 is conceptually and functionally similar to the device of FIGS. 1A-2 described above, but employs a pressure-compensated flow path located around the periphery of the inflatable reservoir rather than in its center.

Thus, device 60 has a first portion 62, formed primarily from elastomeric material, having an opening 66, and a closure portion 64 cooperating with opening 66 of first portion 62 so as to complete the inflatable drug reservoir. When assembled, as shown in FIGS. 8C and 8D, closure portion 64 extends into first portion 62, inwards from opening 66, to define at least one region of overlap between first portion 62 and closure portion 64.

The outward-facing surface of closure portion 64 is shown here formed with a peripheral channel 68 following a roughly helical path so that, when coming into overlapping relation with the inward-facing surface of first portion 62, they together define an outlet flow path traversing the region of overlap for releasing a drug from the drug reservoir. It will be appreciated, particularly with reference to FIG. 8E, that the pressure difference between the liquid 132 within the reservoir and that in the flow path acts to modify the cross-section of flow channel 68, thereby changing the flow impedance of the outlet flow path when the pressure within the reservoir varies, thereby providing an at least partially pressure compensated flow regulating mechanism. This mechanism is essentially the same as described above in more detail with reference to FIG. 2. Flow channel 68 preferably terminates at a relatively large outlet channel 70 (FIG. 8B) which releases the regulated drug flow via opening 66. In an alternative implementation, flow channel 68 may be formed on the inward facing surface of first portion 62.

Here too, one or both of first portion 62 and closure portion 64 may advantageously be implemented using a bioresorbable material, such as those mentioned above.

In order to minimize the dead-space wastage at the end of the drug delivery process, device 60 preferably includes a central core 72 deployed within the inflatable drug reservoir and sized to provide pre-tensioning of the inflatable drug reservoir around central core 72. In the preferred example illustrated here, central core is integrally formed with first portion 62. In alternative implementations, the central core may additionally, or alternatively, be combined with closure portion 64.

First portion 62 and closure portion 64 are preferably preformed in order to generate an initial contact pressure between the overlapping surfaces. In the example illustrated here, closure portion 64 is formed with an initially outward-bulging form, whereas first portion 62 is formed with an initially roughly cylindrical outer wall. During assembly, closure portion 64 is inserted under pressure while first portion 62 is temporarily stretched open. When released, first portion 62 presses closure portion 62 inwards, ensuring sufficient initial contact pressure to define the outlet flow path, and closing closure portion 62 against central core 72. The form of the initial biased shape may clearly vary.

Turning now to FIGS. 9A-9D, these illustrate a further variant drug delivery device, generally designated 80, constructed and operative according to an embodiment of the present invention. Device 80 is structurally and functionally analogous to device 70, but is implemented using a single integrally-formed component.

Thus, in this case, closure portion 64 is implemented as a hollow cylindrical extension of the solid central core 72, which is concentrically surrounded by a cylindrical cup-shaped first portion 62. It will be appreciated that the unitary structure of FIG. 9A may readily be formed by standard elastomer production techniques, such as suitable molding techniques.

Device 80 is prepared for use, referred to also as "assembly" of the device, by inverting the sleeve of closure portion 64 while temporarily stretching open first portion 62 so that first portion then closes against the inverted surface of closure portion 64 which has flow channel 68, as seen in FIG. 913. Device 80 is then filled with liquid 132 by injection with a filling needle 130 (see FIG. 9D) to achieve the filled state of FIG. 9C.

Turning now to FIGS. 10A-18B, it should be noted that above-mentioned options of superficial channels and bulk use of porous materials to define flow channels for controlling rates of drug release are not mutually exclusive, and are not exclusive of other techniques for defining flow channels within one of the device portions or between the portions. Particularly for certain very low flow-rate implementations, it may be preferable to implement an effect similar to a porous material (i.e., multiple very small flow paths) without using bulk material with porous properties for any of the components. This may be achieved by creating a multi-channel flow path layer, for example, by providing at least one of the facing surfaces with a roughened or otherwise textured surface, or by providing a coating or other thin layer of porous material. Examples of these options will now be discussed.

FIGS. 10A-15C illustrate a further drug delivery device, generally designated 82, constructed and operative according to an embodiment of the present invention, illustrating the use of a multi-channel flow path layer formed by a rough or textured surface adjacent to a facing surface which is typically but not necessarily smooth. Device 82 as shown here is generally similar to the embodiment of FIGS. 1A-1D described above, having an elastomeric component, including an inflatable bladder-type reservoir 84 with a pierceable septum 84a and a regulator sleeve 84b, cooperating with an insert 86. As best seen in the enlarged views of FIGS. 12B, 13B and 14C, the outward facing surface of insert 86 is here formed with a textured surface of bumps or otherwise raised regions 88a and hollows or otherwise recessed regions 88b which, when located in facing relation to the surface of regulator sleeve 84b define a multitude of fine, interconnecting passageways which together define a multi-channel flow path layer. It will be noted that the flexible regulator sleeve 84b is pressed into a varying degree of intimate contact with this textured surface, thereby providing pressure-responsive flow regulation in the manner described above with reference to FIG. 2.

Figure 14A:
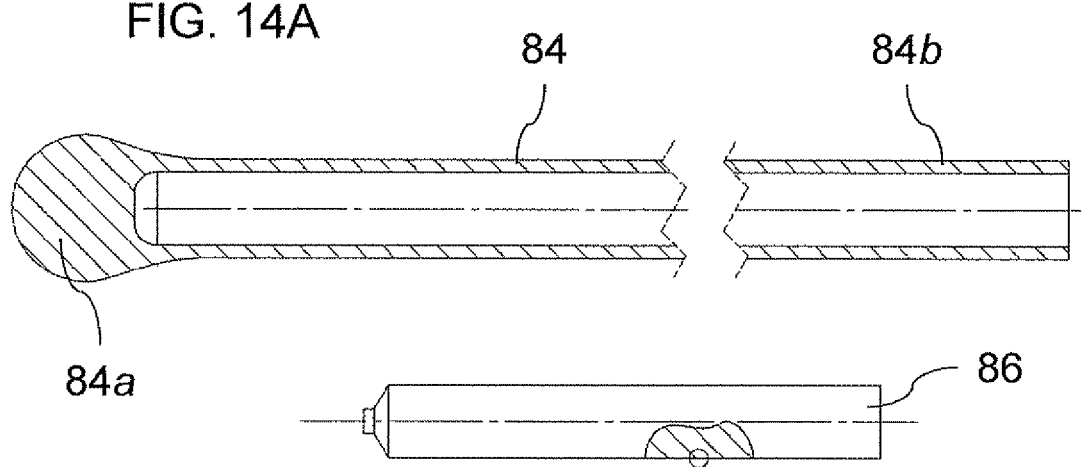
FIGS. 14A and 14B are schematic cross-sectional views taken through an elastomeric component and an insert from the device of FIG. 10A, respectively.
Figure 14B:
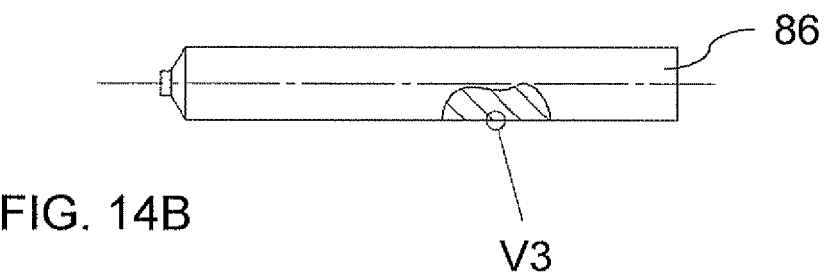
Figure 14C:
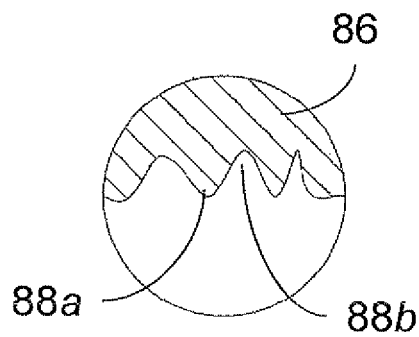
FIGS. 14C and 14D are enlarged views of a circular region of FIG. 14B designated V3 according to two different optional implementations.
Figure 14D:
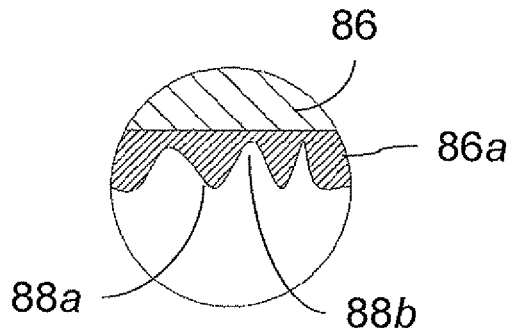
Figure 15A:
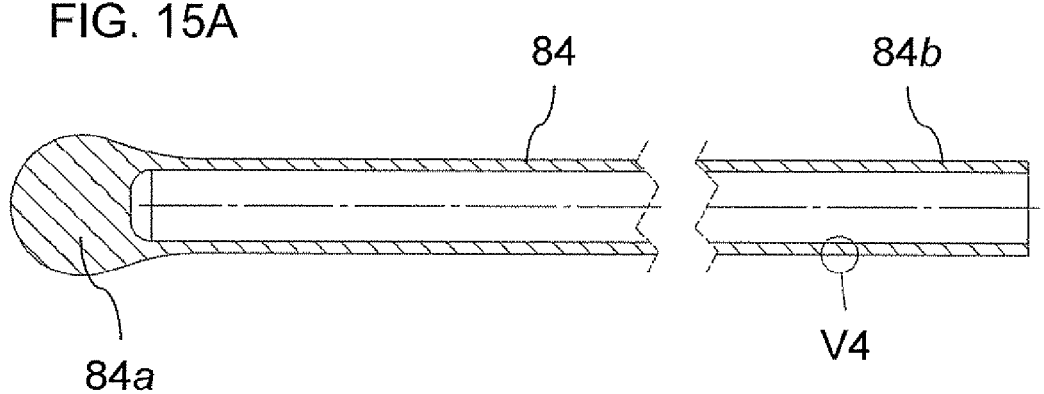
FIG. 15A is a schematic cross-sectional view taken through an elastomeric component and an insert from the device of FIG. 10A according to a further option.
Figure 15B:
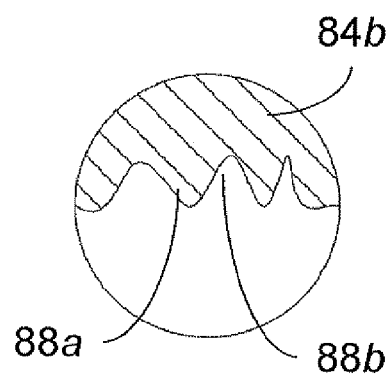
FIGS. 15B and 15C are enlarged views of a circular region of FIG. 15A designated V4 according to two different optional implementations.
Figure 15C:
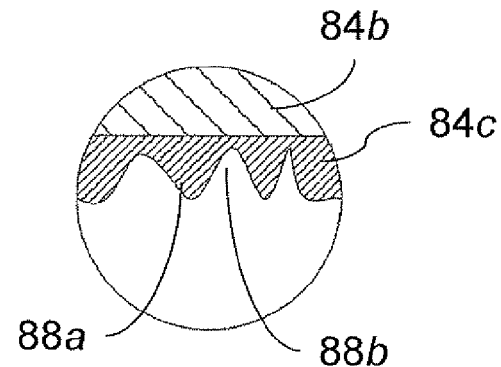

The textured surface of insert 86 may be integrally formed with the body of the insert, as illustrated in FIG. 14C, or may be provided as part of a surface coating or other layer 86a, as illustrated in FIG. 14D. Furthermore, the textured surface may alternatively (or in some cases additionally) be formed as part of the surface of regulator sleeve 84b, such as is illustrated in FIGS. 15A-15B (integrally formed) and 15C (in a coating or supplementary layer 84c). Parenthetically, the textured surface is illustrated as being on the outward facing surface of regulator sleeve 84b since the sleeve is shown in a straightened state, and is inverted over insert 86 when assembled.

The textured surface may be a repeated geometrical pattern, or may be a random or pseudorandom pattern. The pattern may be formed simultaneously as part of the manufacturing process of the component, such as by using a mold with suitably textured surfaces, or may be generated by post-processing, such as by sand-blasting. In the case of a dedicated layer, the texturing may be formed as part of a deposition process for applying the layer.

Turning now to FIGS. 16A-18B, these illustrate a further drug delivery device, generally designated 90, constructed and operative according to an embodiment of the present invention, illustrating the use of a multi-channel flow path layer formed by a porous layer. The implementation illustrated here is conceptually similar to the embodiment of FIG. 5 described above, employing a conical insert 92. In this case, the inner part of insert 92 is formed from a non-porous (e.g., solid or closed-pore) material provided with a layer 94 of porous material. Layer 94 is typically a surface layer, although one or more internal layers may additionally or alternatively be used. Geometrical forms other than conical (e.g., cylindrical or similar to that of FIG. 6 above) may also be used. Other components of device 90 are generally similar to those of device 82 described above, and are numbered similarly.

The layer of porous material may be formed by any suitable production technique, including but not limited to bi-component injection molding, introduction of an inert core into an extruded sleeve of porous material, and various deposition techniques. One non-limiting example of a suitable porous material is porous polyurethane foam.

Figure 18A:
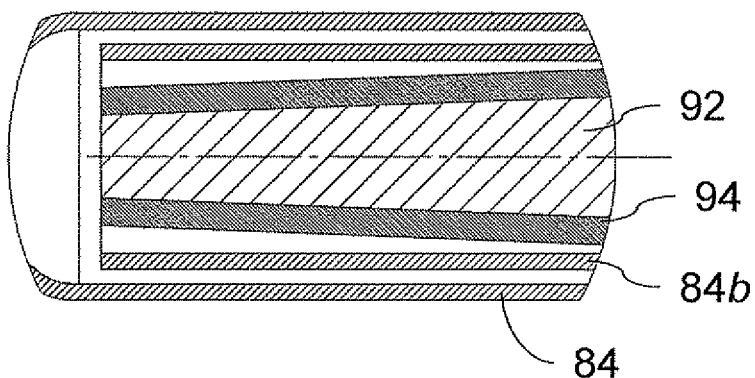
FIGS. 18A and 18B are enlarged views of the regions of FIGS. 16A and 16B designated V11 and V12, respectively.
Figure 18B:
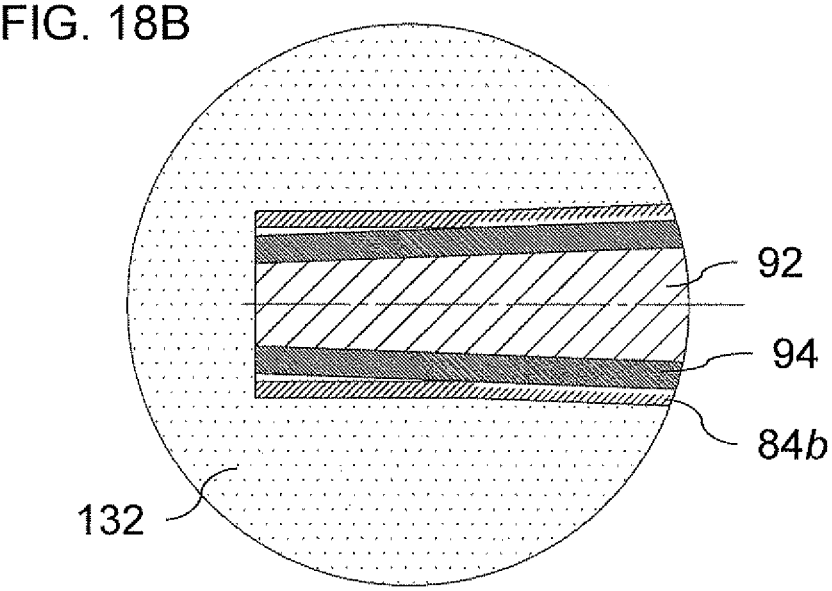

The pressure-responsive flow regulation function is typically achieved by variation in the length of the bypass flow path between the narrow portion of insert 92 and regulator sleeve 84b, in a manner similar to that described above with reference to FIG. 5. The differing degrees of fitting of regulator sleeve 84b to insert 92 in the empty state and full state of the reservoir are illustrated in FIGS. 18A and 18B, respectively. Additionally, or alternatively, in some cases, flow impedance through the porous layer itself may change as the layer is squeezed. Using the latter mechanism, flow regulation may be provided even in a cylindrical geometry (not shown).

In either the textured-surface implementation or the porous layer implementation, the surface properties may optionally be adjusted or modified by application of a suitably chosen thickness of a conformal coating, such as a Parylene coating.

Figure 11A:
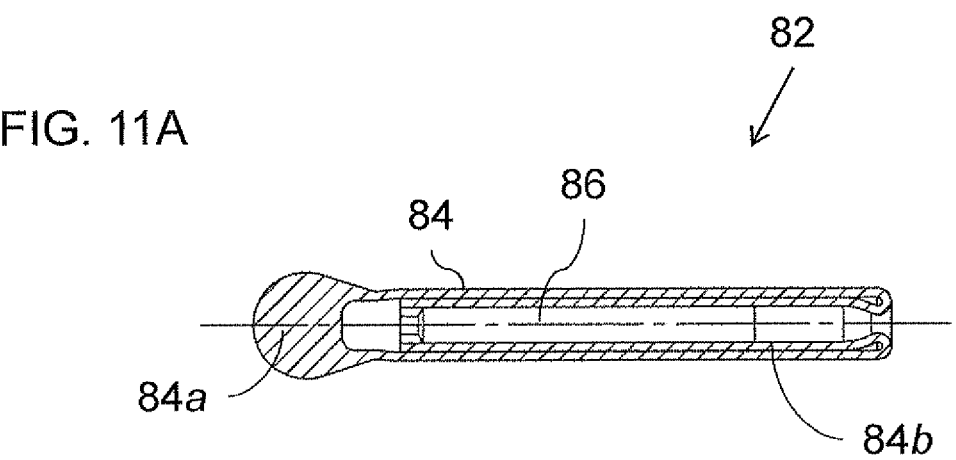
FIGS. 11A and 11B are cross-sectional views taken along the lines X3-X3 of FIG. 10A and X4-X4 of FIG. 10B, respectively.
Figure 11B:
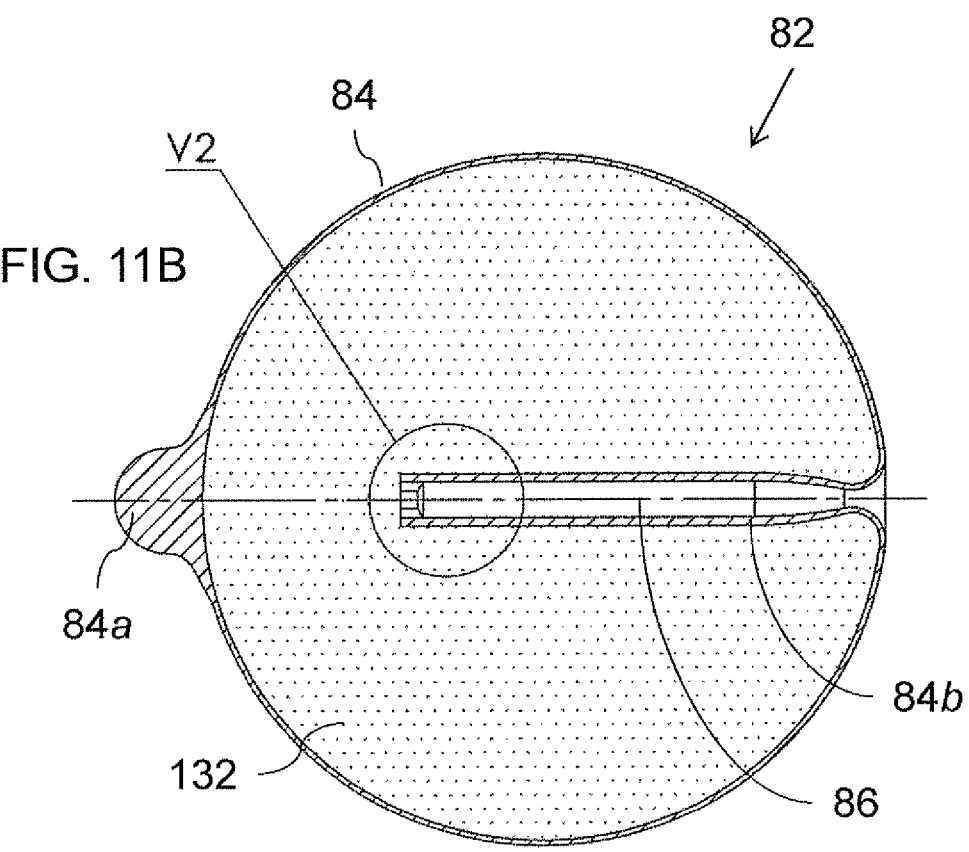
Figure 12B:
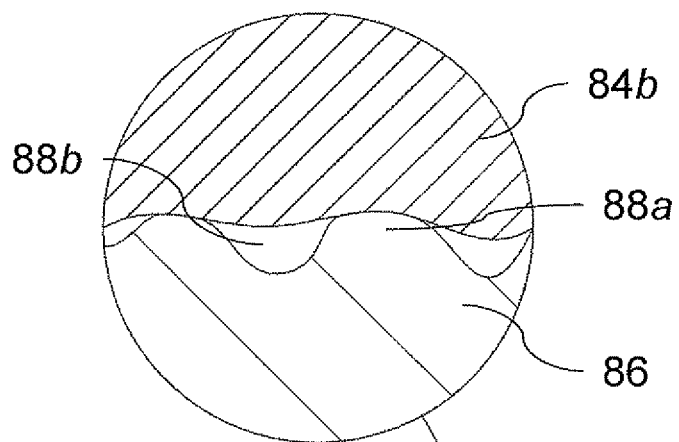
FIG. 12B is a further enlarged view of a circular region of FIG. 12A as indicated.
Figure 12A:
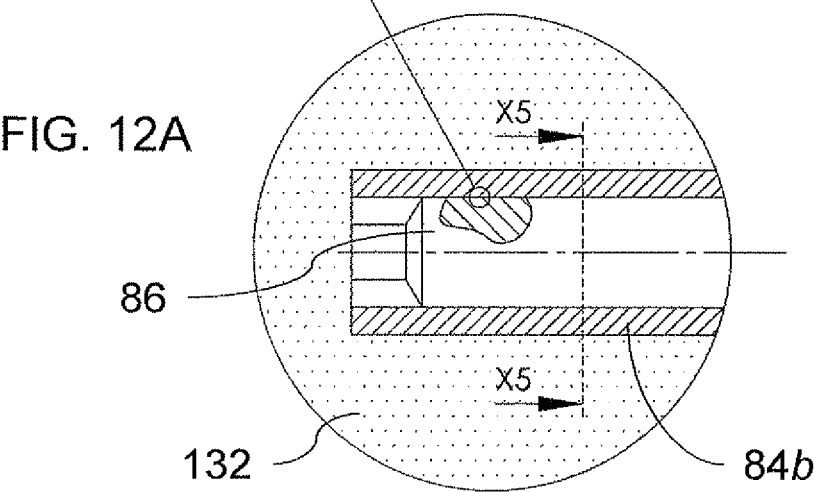
FIG. 12A is an enlarged view of a region of FIG. 11B designated. V2.
Figure 16A:
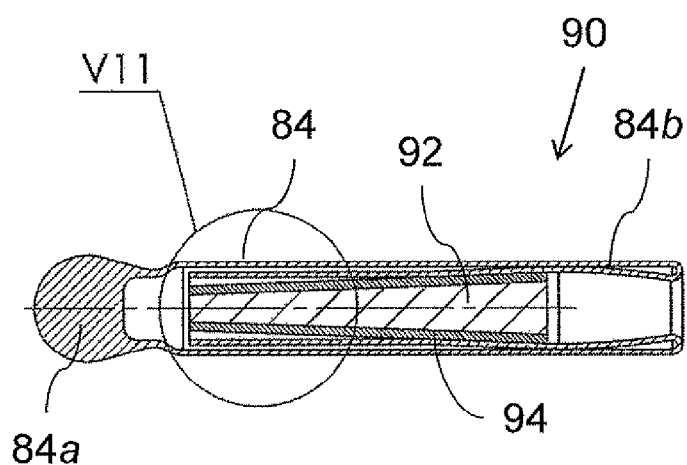
FIGS. 16A and 16B are schematic cross-sectional views taken through a drug delivery device according to an embodiment of the present invention, shown in an empty and a full state, respectively.
Figure 16B:
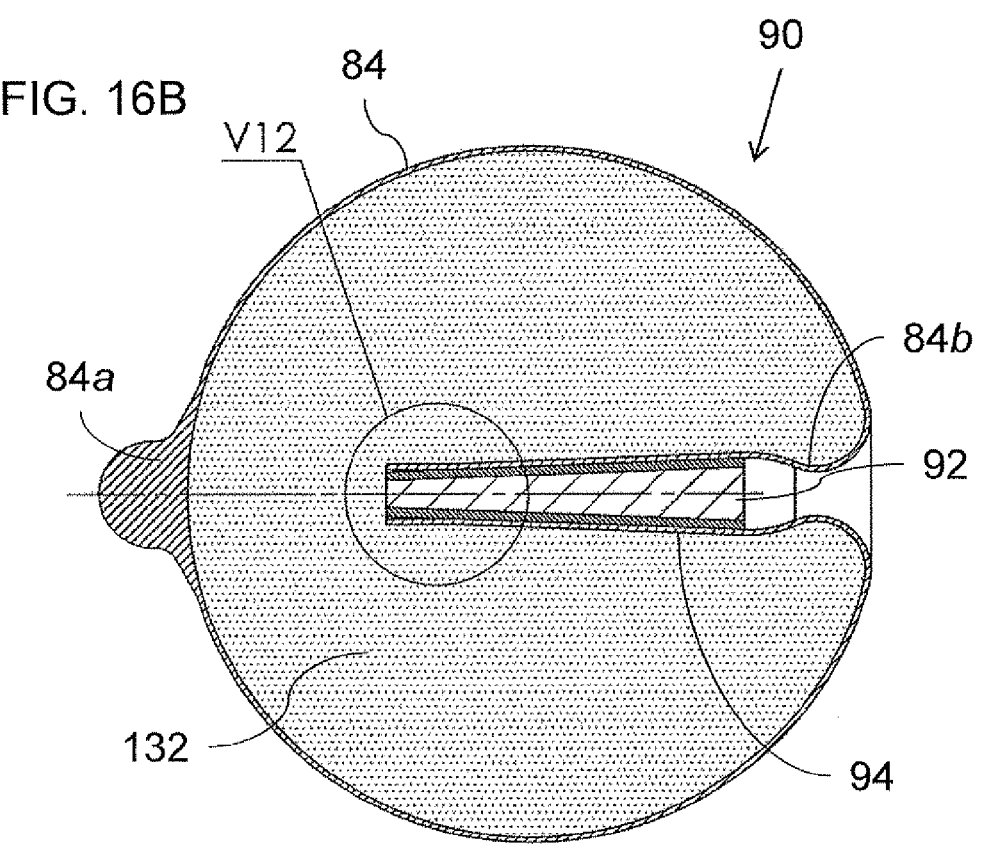
Figure 17:
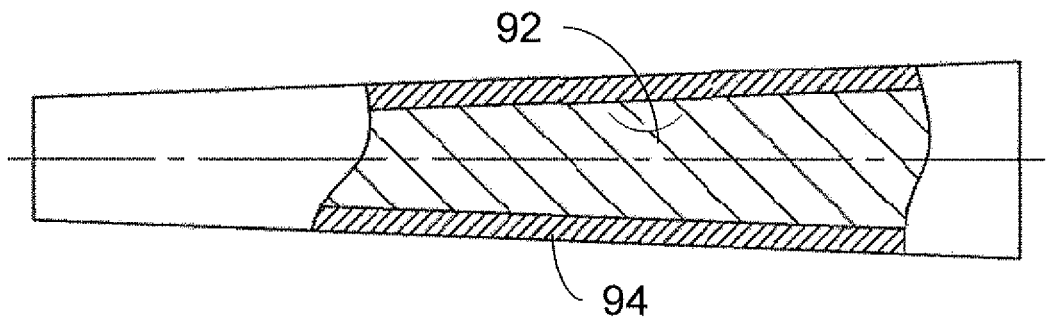
FIG. 17 is a partially cut-away view of an insert from the drug delivery device of FIGS. 16A and 16B.

Parenthetically, it will be noted that the embodiments illustrated in FIGS. 11B and 16B achieve a stable configuration even without the presence of any retaining bead. This is the achieved by employing an insert which is shorter than the extent of the inverted part of regulator sleeve 84b, thereby creating a narrowed neck portion where the pressure within the reservoir acts to constrict the outlet to dimensions smaller than the diameter of the insert, thereby preventing egress of the insert.

Turning now to FIGS. 19A-24, these illustrate a number of additional embodiments of the principles of the present invention. Particularly for applications requiring very low flow rates of drug release, production techniques for components defining correspondingly fine flow channels with sufficient precision may become increasingly complex and expensive. As an alternative approach, this aspect of the present invention provides various arrangements defining a fine liquid flow path formed by clearance spaces around or within a thread deployed within, or adjacent to, a resilient material.

The term "thread" is used herein in the description and claims to refer to any thread, strand, filament, fiber, string, cord, wire, braid or the like, independent of the material from which it is made, whether naturally occurring or synthetic, and having any cross-sectional shape. The term "thread" is used herein generically for multi-filament structures, formed from multiple fibers or filaments twisted together or otherwise combined, as well as for mono-filament structures, formed from a monolithic elongated fiber or wire. It is clarified herein that the term "thread" thus defined encompasses also glass-fibers, mineral wool fibers, metal fibers and hairs. Particularly preferred but non-limiting examples include stainless steel wire and medical stitching thread ("suture" material).

Thus, referring to FIGS. 19A-19C, there is shown a drug delivery device 250 having a reservoir 252 for containing a quantity of liquid drug to be released and a flow path in fluid connection with the reservoir and configured to convey a flow of the liquid drug from the reservoir for delivery to a user. In the case shown here, a thread 254 passes between a first surface, provided by the outer surface of a plug 256, and a layer 258 of resilient material, here formed as an elastic sleeve stretched around plug 256 so as to be biased into close contact with the first surface. In the particularly preferred case illustrated here, elastic sleeve 258 is integrally formed with an inflatable bladder-type reservoir 252, rendering the structure particularly simple.

The enlarged view of FIG. 19C illustrates how the presence of thread 254 generates clearance spaces 260 between the elastic sleeve 258 and the surface of plug 256. Specifically, the elastic properties of elastic sleeve 258 cause it to partially deform around thread 254 but clearly do not allow complete closure of the narrow roughly triangular gaps forming clearance spaces 260. Furthermore, the dimensions of these gaps are primarily defined by the dimensions of thread 254 and the bulk properties of the adjacent material(s), which are relatively easy parameters to control. Additionally, the clearance spaces are typically relatively small compared to the thread thickness. These factors together render this structure suitable for achieving very fine flow channels in a repeatable and precise manner and without complex or expensive production techniques.

According to a further preferred feature of certain embodiments of the present invention as exemplified here, layer 258 of resilient material is deployed so as to be acted upon by a liquid pressure within reservoir 252. Variations in pressure acting on layer 258 tend to make it conform slightly more or slightly less to the surface of thread 254, thereby changing the cross-sectional size of the clearance spaces 260. This provides pressure responsive regulation of dimensions of the clearance spaces, and hence of a flow rate along the flow path.

Turning now to FIGS. 20-22C, these illustrate alternative implementations of this aspect of the present invention according to which thread 254 passes through a block 262 of the resilient material. In this case, if the thread passes through a round cross-section opening (for example, an opening formed by forcing a round cross-section needle through the block), a multi-filament thread is preferably used, thereby inherently providing fine clearance spaces between the filaments making up the thread, and hence forming the required flow-regulating flow path.

Figure 22A:
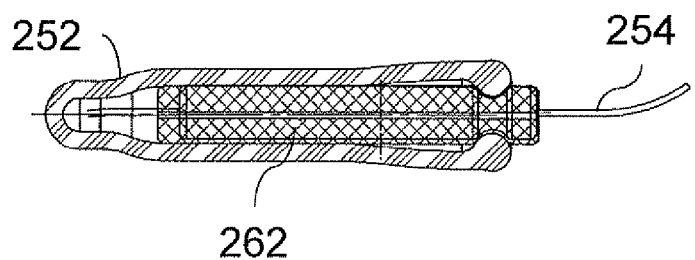
FIGS. 22A and 22B are schematic cross-sectional views of a further alternative implementation of a drug delivery device based upon use of a thread to define a narrow flow passageway, constructed and operative according to an embodiment of the present invention, the device being shown in its empty and filled states, respectively.
Figure 22B:
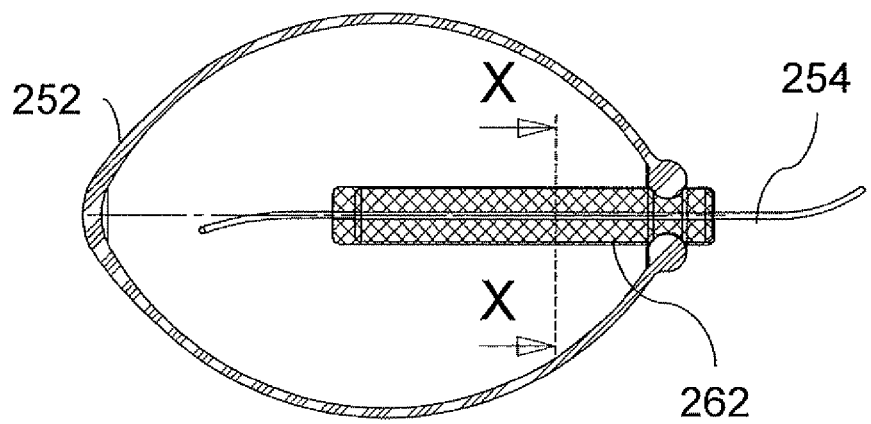
Figure 22C:
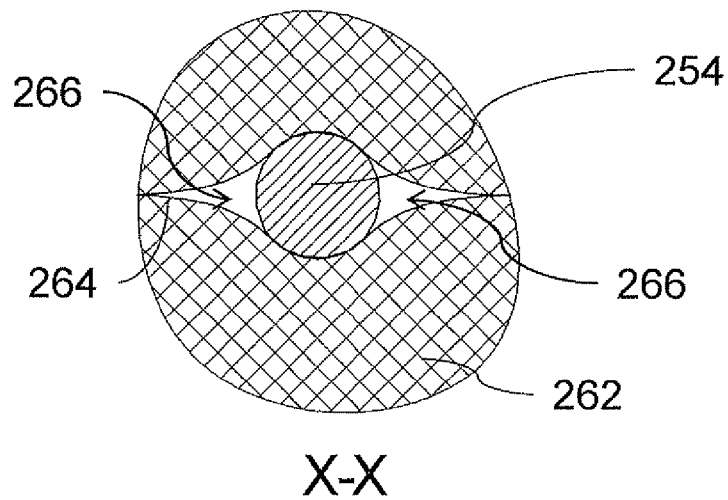
FIG. 22C is a partial schematic cross-sectional view taken along the line X-X of FIG. 22B, showing a region around the central thread according to one possible implementation of the drug device of FIG. 22B.

Alternatively, thread 254 may be deployed passing between inward-facing surfaces 264 of a flat slit cut through block 262 of resilient material, as illustrated in FIG. 22C, thereby forming small triangular clearance spaces 266 structurally and functionally similar to clearance spaces 260 of FIG. 19C.

Figure 20:
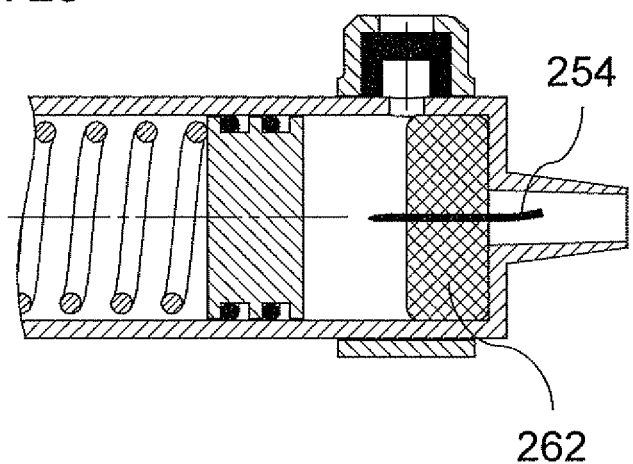
FIG. 20 is a schematic cross-sectional view of an alternative implementation of a drug delivery device based upon use of a thread to define a narrow flow passageway, constructed and operative according to an embodiment of the present invention.
Figure 21:
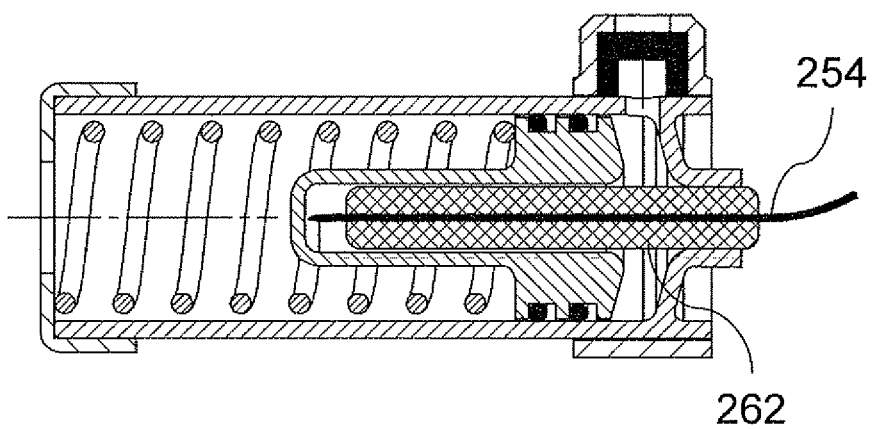
FIG. 21 is a schematic cross-sectional view of a further alternative implementation of a drug delivery device based upon use of a thread to define a narrow flow passageway, constructed and operative according to an embodiment of the present invention.

It will be noted that the principles of this aspect of the present invention may be employed in many different types of drug delivery devices. Thus, by way of non-limiting examples, FIGS. 20 and 21 illustrate two types of syringe-based-reservoir devices. FIGS. 22A-22C relate to a device generally similar to that of FIG. 20 in overall structure. However, in this case, since the thread passes within the block of resilient material, no elastic sleeve is typically required around the block.

Here too, it should be noted that the thread-based drug release flow path preferably provides pressure responsive flow regulation. In the cases of FIGS. 21 and 22A-22C, the outer surface of the long cylindrical block is clearly exposed to the reservoir pressure, thereby applying inward pressure to modify the dimensions of clearance spaces 266 (or spaces between filaments within the thread, not shown), in a manner analogous to that described above. In the case of FIG. 20, increased pressure on the large surface of block 262 tends to make the block spread in the perpendicular direction, and is therefore also effective to apply inward pressure on the clearance spaces to achieve pressure-responsive flow rate regulation.

Figure 23A:
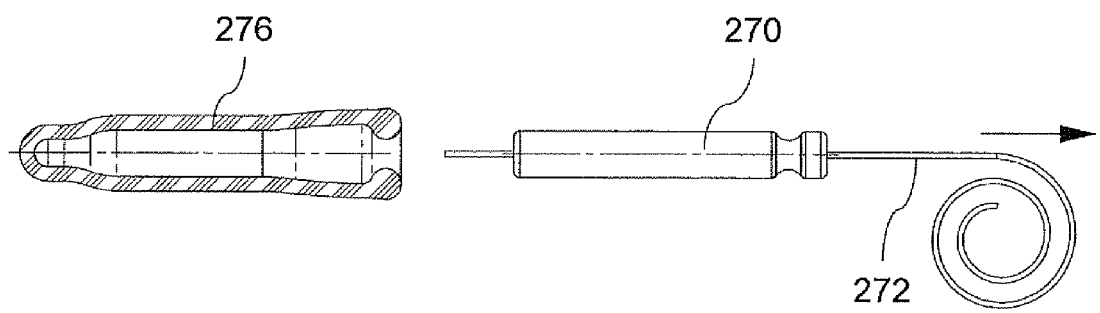
FIGS. 23A-23C are schematic cross-sectional views of a drug delivery device according to a further aspect of the present invention, the device being shown prior to assembly and in its empty and filled states, respectively.
Figure 23B:
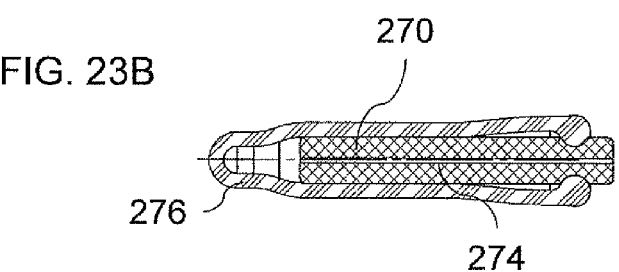
Figure 23C:
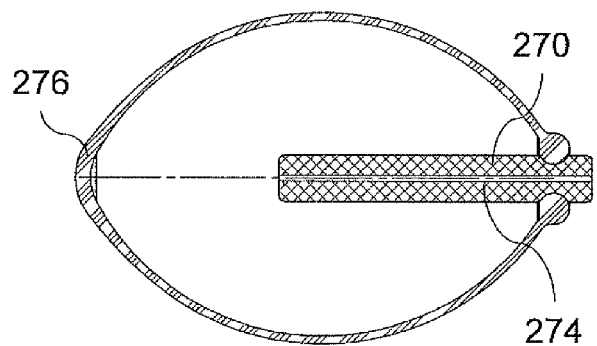
Figure 24:
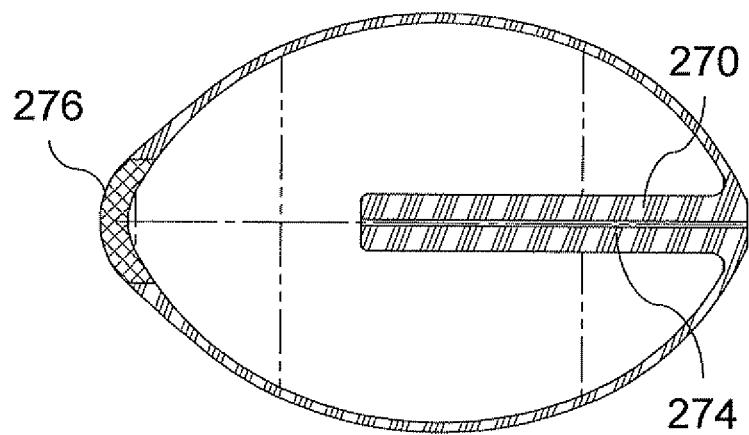
FIG. 24 is a schematic cross-sectional view of an alternative implementation of the device of FIG. 23C.

Turning finally to FIGS. 23A-24, these show a further aspect of the present invention according to which a fine, precise open bore though a resilient block of material can be produced cheaply and repeatably. In this case, a block 270 is formed, typically by injection molding, with a fine wire 272 extending through the block. After the block is formed and cooled or cured, the wire is removed by drawing it out of the material, leaving a well defined open bore 274 through block 270. Block 270 can then be used together with a reservoir 276 to four a drug delivery device as shown in FIGS. 23B and 23C, where bore 274 provides the fine flow path required. FIG. 24 shows a similar structure where block 270 is integrally formed with reservoir 276.

It should be noted that the above technique for forming a fine bore may also be used as an intermediate production stage with subsequent introduction of a thread into the bore to form a drug delivery device according to the previously described aspect of the present invention.

Finally, turning briefly to FIG. 7, it should be noted that the various embodiments of the invention described herein are not limited to implantable drug delivery devices and can also be implemented to advantage in external drug delivery devices. By way of one non-limiting example, FIG. 7 illustrates a device similar to that of FIG. 5 provided with a needle adapter 40 and adhesive pad 42 for use as an externally skin-mounted drug infusion device. It will be appreciated that this option may be implemented with any and all of the embodiments described herein, or combinations thereof.

It will be appreciated that the above descriptions are intended only to serve as examples, and that many other embodiments are possible within the scope of the present invention as defined in the appended claims.

What is claimed is:

1. A drug delivery device providing a drug reservoir integrated with an at least partially pressure-compensated flow regulating mechanism, the drug delivery device comprising:
   (a) a first portion formed primarily from elastomeric material, said first portion at least partially defining an inflatable drug reservoir, said first portion having an opening and a flexible sleeve extending inwards from said opening; and
   (b) a closure portion cooperating with said opening of said first portion so as to complete said inflatable drug reservoir, wherein said closure portion is implemented as an insert inserted within said flexible sleeve so as to provide a region of overlap between said first portion and said closure portion, said insert being sized to provide pre-tensioning of said inflatable drug reservoir around said insert, and wherein said first portion and said closure portion define an outlet flow path for releasing a drug from said drug reservoir, at least part of said outlet flow path passing between said first portion and said closure portion in said region of overlap, said region of overlap being disposed so as to be acted upon by a pressure within said drug reservoir so as to change a flow impedance of said outlet flow path when the pressure within the reservoir varies, thereby providing an at least partially pressure compensated flow regulating mechanism.

2. The drug delivery device of claim 1, wherein at least one of said first portion and said closure portion is provided with features for defining a multi-channel flow path layer.

3. The drug delivery device of claim 2, wherein said features include a textured surface.

4. The drug delivery device of claim 2, wherein said features include a porous layer.

5. The drug delivery device of claim 1, wherein one of said first portion and said closure portion is provided with an elongated channel deployed to define at least part of said flow path through said region of overlap.

6. A drug delivery device providing a drug reservoir integrated with an at least partially pressure-compensated flow regulating mechanism, the drug delivery device comprising:
   (a) a first portion formed primarily from elastomeric material, said first portion at least partially defining an inflatable drug reservoir, said first portion having an opening; and
   (b) a closure portion cooperating with said opening of said first portion so as to complete said inflatable drug reservoir, wherein said closure portion extends into said first portion inwards from said opening to define at least one region of overlap between said first portion and said closure portion, and wherein said first portion and said closure portion define an outlet flow path for releasing a drug from said drug reservoir, at least part of said outlet flow path passing between said first portion and said closure portion in said region of overlap, said region of overlap being disposed so as to be acted upon by a pressure within said drug reservoir so as to change a flow impedance of said outlet flow path when the pressure within the reservoir varies, thereby providing an at least partially pressure compensated flow regulating mechanism, the drug delivery device further comprising a thread extending through said region of overlap such that clearance spaces around or within said thread define at least part of said flow path through said region of overlap.

7. The drug delivery device of claim 1, wherein said insert is formed primarily from a porous material.

8. The drug delivery device of claim 7, wherein said insert and said flexible sleeve are configured such that an extent of contact between said flexible sleeve and said insert varies as a function of the pressure within said inflatable drug reservoir.

9. The drug delivery device of claim 1, wherein said insert is formed with an elongated circumferential channel.

10. The drug delivery device of claim 1, wherein said insert is formed primarily from a bioresorbable material.

11. The drug delivery device of claim 1, wherein at least said first portion is formed from silicone.

12. The drug delivery device of claim 1, wherein at least one of said first portion and said closure portion is formed from a bioresorbable material.

13. The drug delivery device of claim 1, wherein said first portion and said closure portion are formed as two separate components.

14. The drug delivery device of claim 1, wherein said first portion and said closure portion are integrally formed, and wherein the drug delivery device is assembled by inverting at least said flexible sleeve so as to generate said region of overlap.

15. The drug delivery device of claim 1, wherein said insert is implemented as a central core deployed within said inflatable drug reservoir.

16. The drug delivery device of claim 1, further comprising a septum integrated with said first portion for piercing by a needle during filling of said inflatable drug reservoir, wherein said septum projects into said inflatable drug reservoir.

17. The drug delivery device of claim 6, wherein said thread is interposed between a surface of said first portion and a surface of said closure portion in said region of overlap.

18. The drug delivery device of claim 6, wherein said thread is a monofilament thread.

* * * * *